US007326767B1

(12) United States Patent
Stauss et al.

(10) Patent No.: US 7,326,767 B1
(45) Date of Patent: Feb. 5, 2008

(54) IMMUNOTHERAPEUTIC METHODS USING EPITOPES OF WT-1 AND GATA-1

(75) Inventors: Hans Josef Stauss, London (GB); Liquan Gao, Ilford (GB)

(73) Assignee: Ganymed Pharmaceuticals, AG (DE)

( * ) Notice: Subject to any disclaimer, the term of this patent is extended or adjusted under 35 U.S.C. 154(b) by 0 days.

(21) Appl. No.: 09/625,963

(22) Filed: Jul. 26, 2000

Related U.S. Application Data

(63) Continuation of application No. PCT/GB99/03572, filed on Nov. 2, 1999.

(30) Foreign Application Priority Data

Nov. 2, 1998 (GB) .................................. 9823897.5

(51) Int. Cl.
| C07K 7/00 | (2006.01) |
| C07K 14/00 | (2006.01) |
| A61K 38/00 | (2006.01) |
| A61K 38/03 | (2006.01) |

(52) U.S. Cl. ................ 530/300; 424/185.1; 424/277.1; 514/12; 514/13; 514/14; 514/15; 530/324; 530/325; 530/326; 530/327; 530/328

(58) Field of Classification Search ................ 530/300, 530/328, 324, 325, 326, 327; 514/15, 12, 514/13, 14; 424/185.1, 277.1
See application file for complete search history.

(56) References Cited

U.S. PATENT DOCUMENTS

| 5,726,288 A | 3/1998 | Call et al. |
| 5,731,160 A | 3/1998 | Molief |
| 2003/0082196 A1* | 5/2003 | Gaiger et al. ............. 424/185.1 |

FOREIGN PATENT DOCUMENTS

| JP | 10 218093 | 7/1999 |
| WO | WO91/17509 A1 | 5/1991 |
| WO | WO95/29995 A1 | 11/1995 |
| WO | WO97/26328 A1 | 7/1997 |
| WO | WO 00/06602 A1 | 2/2000 |
| WO | WO 00/18795 A2 | 4/2000 |

OTHER PUBLICATIONS

Janeway et al Immunobiology, 1997 4th Edition Garland Press 1999 pp. 121, 551 and 569 and Figures 4.3, 4.5 and 4.7.*
Semba et al. Gene 175:167-172, 1996.*
Sharma et al. Cancer Res. 52:6407-64112, 1992.*
Buckler et al. Mol. Cell. Biol. 11:1701-1712, 1991.*
Bluyssen et al Eur. J. Biochem. 220:395-02, 1994.*
Oka, Y. et al. J. Immunol. [Feb. 15, 2000] 164(4):1873-1880.*
Mailander, V. et al. Leukemia (2004) 18:165-166.*
Gaiger, A. et al. Blood (2000) 96(4):1480-1489.*
Morel, S. et al. Immunity [Jan. 2000] 12:107-117.*
Al-Odeidi, et al., "Peptide and peptidomimetic libraries," *Molecular Biotechnology* 9:205-223 (1998).
Beeley, "Peptidomimetics and small-molecule drug design: towards improved bioavailability and in vivo stability," *TIBTECH* 12:213-216 (1994).
Bottger, et al., "Molecular characterization of the hdm2-p53 interaction," *J Mol Biol* 269:744-756 (1997).
Crossley & Orkin, "Phosphorylation of the Erythroid Transcription Factor GATA-1," *J Bio Chem* 269:16589-96 (1994).
Gaiger, et al., "Immunity to WT1 in the animal model and in patients with acute myeloid leukemia," *Blood* 96(4):1480-89 (2000).
Gao, et al., "Selective elimination of leukemic CD34+ progenitor cells by cytotoxic T lymphocytes specif for WT1," *Blood* 95:2198-2203 (2000).
Kieber-Emmons, et al., "Therapeutic peptides and peptidomimetics," *Curr Opinion Biotechnol* 8:436-441 (1997).
Meziere, et al., "In vivo helper cell response to retro-inverso peptidomimetics," *Journal of Immunology* 159:3230-37 (1997).
Murali & Greene, "Structure-based design of immunologically active therapeutic peptides," Immunolgic Research 17(1&2):163-169 (1998).
Nakanishi, et al., "Peptidomimetics of the immunolglobin supergene family—a review," *Gene* 137:51-56 (1993).
Ohminami, et al., "HLA class I-restricted lysis of leukemia cells by a CD8+ cytotoxic T-lymphocyte clone specific for WT1 peptide," *Blood* 95:286-93 (2000).
Oka, et al., "Cancer immunotherapy targeting Wilms' Tumor Gene WT1 product," *J Immunol* 164:1873-80 (2000).
Oka, et al., "Human cytotoxic T-lymphocyte responses specific for peptides of the wild-type Wilms tumor (WT1) product," *Immunogenetics* 51:99-107 (2000).
Sadovnikova & Stauss, "Peptide-specific cytotoxic T lymphocytes restricted by nonself major histocompatibility complex class I molecules: reagents for tumor immunotherapy," *Proc Natl Acad Sci USA* 93:13114-13118 (1996).
Algar, et al., "A WT1 antisense oligonucleotide inhibits proliferation and induces apoptosis in myeloid leukemia cell lines," Oncogene 12: 1005-1014 (1996).
Baird, et al., "Expression of the Wilms' tumor gene (WT1) in normal hemopoiesis," Exp. Hematol. 25: 312-320 (1997).
Bhatia, et al., "A newly discovered class of human hematopoietic cells with SCID-repopulating activity," Nature Med. 4: 1038-1045 (1998).
Bonnet & Dick, "Human acute myeloid leukemia is organized as a hierarchy that originates from a primitive hematopoietic cell," Nature Med. 3: 730-737 (1997).

(Continued)

*Primary Examiner*—Christina Chan
*Assistant Examiner*—F. Pierre VanderVegt
(74) *Attorney, Agent, or Firm*—Olson & Hierl, Ltd.

(57) ABSTRACT

A peptide comprising the amino acid sequence RMFP-NAPYL (SEQ ID NO:1) or a portion or variant thereof provided that the peptide is not intact human WT-1 polypeptide or a peptide comprising the amino acid sequence CMTWNQMNL (SEQ ID NO:2) or a portion or variant thereof provided that the peptide is not intact human WT-1 polypeptide or a peptide comprising the amino acid sequence HLMPFPGPLL (SEQ ID NO:3) or a portion or variant thereof provided that the peptide is not intact human gata-1 polypeptide, and polynucleotides encoding these peptides. The peptides and polynucleotides are useful as cancer vaccines.

4 Claims, 9 Drawing Sheets

OTHER PUBLICATIONS

Figure 1:
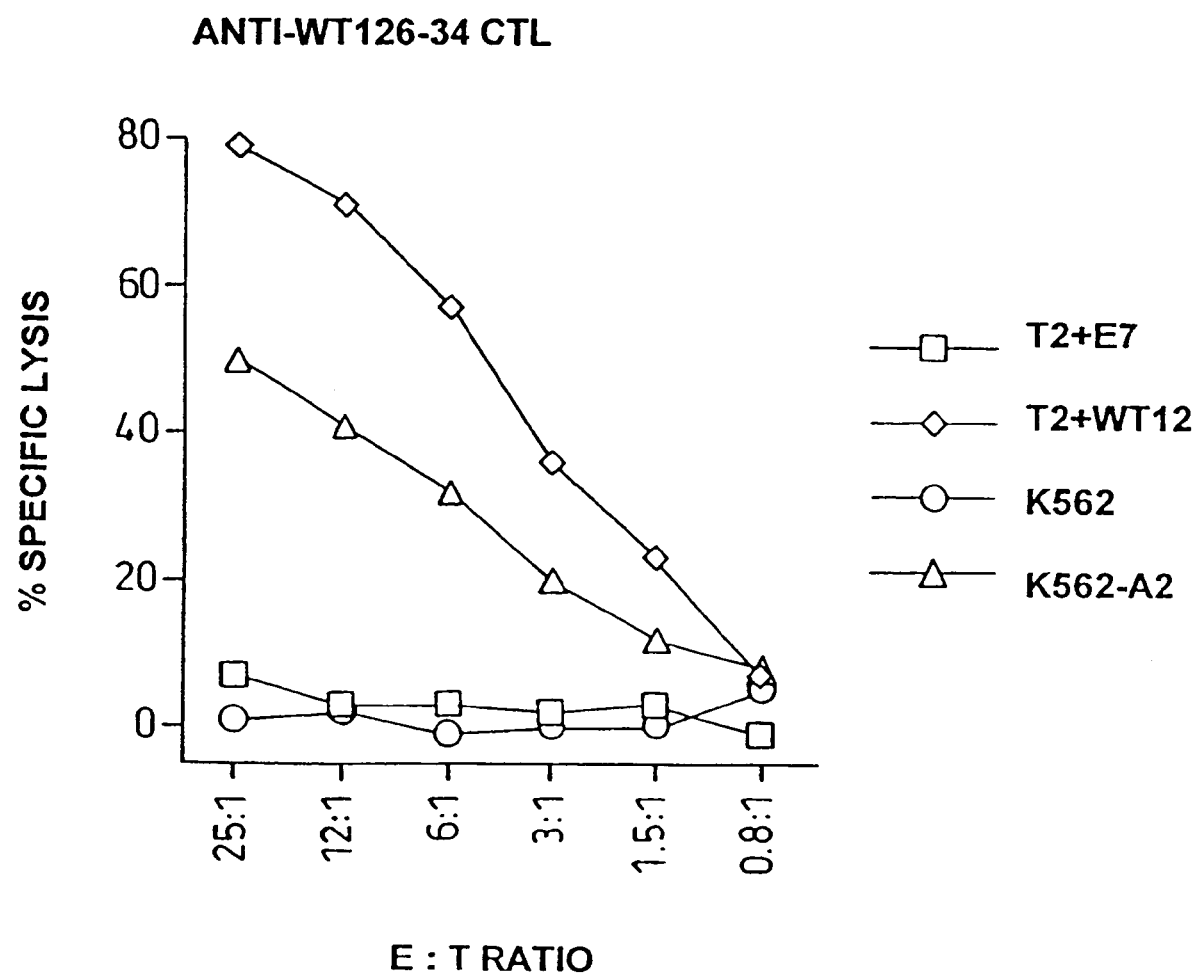

Bose, et al., "The presence of typical and atypical BCR-ABL fusion genes in leukocytes of normal individuals: biologic significance and implications for the assessment of minimal residual disease," Blood 92: 3362-3367 (1998).

Campbell, et al., "Constitutive expression of the Wilms tumor suppressor gene (WT1) in renal cell carcinoma," Int. J. Cancer 78: 182-188 (1998).

Dazzi & Goldman, "Adoptive immunotherapy following allogeneic bone marrow transplantation," Ann. Rev. Med. 49: 329-340 (1998).

Dazzi, et al., "The kinetics and extent of engraftment of chronic myelogenous leukemia cells in non-obese diabetic/severe combined immunodeficiency mice reflect the phase of the donor's disease: an in vitro model of chronic myelogenous leukemia biology," Blood 92: 1390-1396 (1998).

Demars, et al., "Homozygous deletion that simulataneously eliminate expression of class I and class II antigens of EBV-transformed B-lymphoblastoid cells. I. Reduced proliferative responses of autologous and allogeneic T cells to mutant cells that have decreased expression of class II antigens," Hum. Immunol. 11: 77-97 (1984).

Den Haan, et al., "The minor histocompatibility antigen HA-1: a diallelic gene with a singe amino acid polymorphism," Science 279: 1054-1057 (1998).

Digiusto, et al., "Human fetal bone marrow early progenitors for T, B, and myeloid cells are found exclusively in the population expressing high levels of CD34," Blood 84: 421-432 (1994).

Findley, Jr., et al., "Two new acute lymphoblastic leukemia cell lines with early B-cell phenotypes," Blood 60: 1305-1309 (1982).

Griffin, et al., "Clonogenic cells in acute myeloblastic leukemia," Blood 68: 1185-1195 (1986).

Inoue, et al., "Aberrant overexpression of the Wilms tumor gene (WT1) in human leukemia," Blood 89: 1405-1412 (1997).

Inoue, et al., "Wilms' tumor gene (WT1) competes with differentiation-inducing signal in hematopoietic progenitor cells," Blood 91: 2969-2976 (1998).

Inoue, et al., "WT1 as a new prognostic factor and a new marker for the detection of minimal residual disease in acute leukemia," Blood 84: 3071-3079 (1994).

Kolb, et al., "Donor leukocyte transfusions for treatment of recurrent chronic myelogenous leukemia in marrow transplant patients," Blood 76: 2462-2465 (1990).

Lozzio & Lozzio, "Human chronic myelogenous leukemia cell-line with positive Philadelphia chromosome," Blood 45: 321-334 (1975).

Maurer, et al, "The Wilms' tumor gene is expressed in a subset of CD34+progenitors and downregulated early in the course of differentiation in vitro," Exp. Hematol. 25: 945-950 (1997).

McCulloch, "Stem cells in normal and leukemic hemopoiesis," Blood 62: 1-13 (1983).

Menke, et al., "The Wilms' tumor 1 gene: oncogene or tumor suppressor gene?" Int. Rev. Cytol. 181: 151-212 (1998).

Molldrem, et al., "Cytotoxic T-lymphocytes specific for a nonpolymorphic proteinase-3 peptide preferentially inhibit chronic myeloid-leukemia colony-forming units," Blood 90: 2529-2534 (1997).

O'Brien & Goldman, "Current approaches to hematopoietic stem-cell purging in chronic myeloid leukemia," J. Clin. Oncol. 13: 541-546 (1995).

Osaka, et al., "WT1 contributes to leukemogenesis: expression patterns in 7,12-dimethylbenz[a]anthracene (DMBA)-induced leukemia," Int. J. Cancer 72: 696-699 (1997).

Pegoraro, et al., "Establishment of a Ph1-positive human cell line (BV173)," J. Natl Cancer. Inst. 70:447-453 (1983).

Petersdorf, et al., "Optimizing outcome after unrelated marrow transplantation by comprehensive matching of HLA class I and II alleles in the donor and recipient," Blood 92: 3515-3520 (1998).

Rodeck, et al., "Expression of the wt1 Wilms' tumor gene by normal and malignant human melanocytes," Int. J. Cancer 59: 78-82 (1994).

Sadovnika, et al., "Generation of human tumor-reactive cytotoxic T cells against peptides presented by non-self HLA class I molecules," Eur. J. Immunol. 28: 193-200 (1998).

Silberstein, et al., "Altered expression of the WT1 Wilms tumor suppressor gene in human breast cancer," Proc. Natl. Acad. Sci. USA 94: 8132-8137 (1997).

Simpson, et al., "Much ado about minor histocompatibility antigens," Immunol. Today 19: 108-112 (1998).

Smit, et al., "T cells recognizing leukemic CD34(+) progenitor cells mediate the antileukemic effect of donor lymphocyte infusions for relapsed chronic myeloid leukemia after allogenic stem cell transplantation," Proc. Natl. Acad. Sci USA 95: 10152-10157 (1998).

Strauss, "Immunotherapy with CTL restricted by non-self MHC," Immunol. Today 20: 180-183 (1999).

Svedberg, et al., "Constitutive expression of the Wilms' tumor gene (WT1) in the leukemic cell line U937 blocks part of the differentiation program," Oncogene 16: 925-932 (1998).

Viel, et al., "Molecular mechanisms possibly affecting WT1 function in human ovarian tumors," Int. J. Cancer 57: 515-521 (1994).

Wang, et al., "High level engraftment of NOD/SCID mice by primitive normal and leukemic hematopoietic cells from patients with chronic myeloid leukemia in chronic phase," Blood 91: 2406-2414 (1998).

Warren, et al., "Minor histocompatibility antigens as targets for T-cell therapy after bone marrow transplantation," Curr. Opin. Hematol. 5: 429-433 (1998).

Yamagami, et al., "Growth inhibition of human leukemic cells by WT1 (Wilms tumor gene) antisense oligodeoxynucleotides: implications for the involvement of WT1 in leukemogenesis," Blood 87: 2878-2884 (1996).

Zemmour, et al., "The HLA-A,B 'negative' mutant cell line C1R expresses a novel HLA-B35 allele which also has a point mutation in the translation initiation codon," J. Immunol. 148: 1941-1948 (1992).

Morris, et al., "Characterization of the zinc finger protein encoded by the WT1 Wilms' tumor locus", Oncogene, 6(12):2339-48 (1991).

Condon, et al., "DNA-based immunization by in vivo transfection of dendritic cells", Nat. Med., 2(10):1122-8 (1996).

Conry, et al., "Polynucleotide-mediated immunization therapy of cancer", Semin. Oncol., 23(1):135-47 (1996).

Gessler, et al., "Homozygous deletion in Wilms tumours of a zinc-finger gene identified by chromosome jumping", Nature, 343(6260):774-8 (1990).

Gong, et al., "Induction of antitumor activity by immunization with fusions of dendritic and carcinoma cells", Nat. Med., 3(5):558-61 (1997).

Graham, et al, "Intramuscular immunisation with MUC1 cDNA can protect C57 mice challenged with MUC1-expressing syngeneic mouse tumour cells", Int. J. Cancer, 65(5):664-70 (1996).

Inoue, et al., "Long-term follow-up of minimal residual disease in leukemia patients by monitoring WT1 (Wilms tumor gene) expression levels", Blood, 88(6):2267-78 (1996).

Kast, et al., "Eradication of adenovirus E1-induced tumors by E1A-specific cytotoxic T lymphocytes", Cell, 59(4):603-14 (1989).

Kawakami, et al., "Identification of a human melanoma antigen recognized by tumor-infiltrating lymphocytes associated with in vivo tumor rejection", Proc. Natl. Acad. Sci. U.S.A., 91(14):6458-62 (1994).

Menssen, et al., "Presence of Wilms' tumor gene (wt1) transcripts and the WT1 nuclear protein in the majority of human acute leukemias", Leukemia, 9(6):1060-7 (1995).

Menssen, et al, "Detection by monoclonal antibodies of the Wilms' tumor (WT1) nuclear protein in patients with acute leukemia", Int. J. Cancer, 70(5):518-23 (1997).

Murphy, et al., "Phase I clinical trial: T-cell therapy for prostate cancer using autologous dendritic cells pulsed with HLA-A0201-specific peptides from prostate-specific membrane antigen", Prostate, 29(6):371-80 (1996).

Ogawa, et al., "Successful donor leukocyte transfusion at molecular relapse for a patient with acute myeloid leukemia who was treated with allogenic bone marrow transplantation: importance of the monitoring of minimal residual disease by WT1 assay", Bone Marrow Transplant, 21(5):525-7 (1998).

Shimamoto, et al., "The expression pattern of erythrocyte/megakaryocyte-related transcription factors GATA-1 and the stem cell leukemia gene correlates with hematopoietic differentiation and is associated with outcome of acute myeloid leukemia", *Blood*, 86(8):3173-80 (1995).

Silberstein, et al., "Altered expression of the WT1 wilms tumor suppressor gene in human breast cancer", *Proc. Natl. Acad. Sci. U.S.A.*, 94(15):8132-7 (1997).

Tjoa, et al., "Follow-up evaluation of prostate cancer patients infused with autologous dendritic cells pulsed with PSMA peptides", *Prostate*, 32(4):272-8 (1997).

Tourdot, et al., "Chimeric peptides: a new approach to enhancing the immunogenicity of peptides with low MHC class I affinity: application in antiviral vaccination", *J. Immunol.*, 159(5):2391-8 (1997).

Viel, et al., "Molecular mechanisms possibly affecting WT1 function in human ovarian tumors", *Int. J. Cancer*, 57(4):515-21 (1994).

Zhai, et al., "Antigen-specific tumor vaccines. Development and characterization of recombinant adenoviruses encoding MART1 or gp100 for cancer therapy", *J. Immunol.*, 158(2):700-10 (1996).

Zon, et al. "The major human erythroid DNA-binding protein (GF-1): primary sequence and localization of the gene to the X chromosome", *Proc. Natl. Acad. Sci. U.S.A.*, 87(2):668-72 (1990).

* cited by examiner

SEQUENCE LISTING

<160> NUMBER OF SEQ ID NOS: 9

<210> SEQ ID NO 1
<211> LENGTH: 9
<212> TYPE: PRT
<213> ORGANISM: Homo sapiens

<400> SEQUENCE: 1

Arg Met Phe Pro Asn Ala Pro Tyr Leu
1               5

<210> SEQ ID NO 2
<211> LENGTH: 9
<212> TYPE: PRT
<213> ORGANISM: Homo sapiens

<400> SEQUENCE: 2

Cys Met Thr Trp Asn Gln Met Asn Leu
1               5

<210> SEQ ID NO 3
<211> LENGTH: 10
<212> TYPE: PRT
<213> ORGANISM: Homo sapiens

<400> SEQUENCE: 3

His Leu Met Pro Phe Pro Gly Pro Leu Leu
1               5                   10

<210> SEQ ID NO 4
<211> LENGTH: 8
<212> TYPE: PRT
<213> ORGANISM: Homo sapiens

<400> SEQUENCE: 4

Thr Leu Gly Ile Val Cys Pro Ile
1               5

<210> SEQ ID NO 5
<211> LENGTH: 9
<212> TYPE: PRT
<213> ORGANISM: Homo sapiens

<400> SEQUENCE: 5

Arg Leu Ser Pro Asp Leu Leu Thr Leu
1               5

<210> SEQ ID NO 6
<211> LENGTH: 21
<212> TYPE: DNA
<213> ORGANISM: Homo sapiens

<400> SEQUENCE: 6
ggcatctgag accagtgaga a                                          21

<210> SEQ ID NO 7
<211> LENGTH: 22
<212> TYPE: DNA
<213> ORGANISM: Homo sapiens

<400> SEQUENCE: 7
gagagtcaga cttgaaagca gt                                         22

```
<210> SEQ ID NO 8
<211> LENGTH: 22
<212> TYPE: DNA
<213> ORGANISM: Homo sapiens

<400> SEQUENCE: 8
cccaaccttt tcgttgcact gt                                              22

<210> SEQ ID NO 9
<211> LENGTH: 22
<212> TYPE: DNA
<213> ORGANISM: Homo sapiens

<400> SEQUENCE: 9
cggctctcgg aggagacgat ga                                              22
```

IMMUNOTHERAPEUTIC METHODS USING EPITOPES OF WT-1 AND GATA-1

This is a continuation of International Application No. PCT/GB99/03572, filed in the United Kingdom Receiving Office for the Patent Cooperation Treaty on Nov. 2, 1999, which claims priority to United Kingdom Application No. GB 9823897.5 filed Nov. 2, 1998.

The present invention relates to immunotherapeutic methods, and molecules and cells for use in immunotherapeutic methods. In particular, the present invention relates to the immunotherapy of cancer including leukaemia.

There is evidence that anti-tumour cytotoxic T lymphocytes (CTL) play an important role in vivo. Tumour reactive CTL have been shown to mediate tumour regression in animal models (Kast et al (1989) *Cell.* 59, 603-614) and in man (Kawakami et al (1994) *Proc. Natl. Acad. Sci. USA* 91, 6458-6462). As with all types of anti-tumour therapy, a problem that needs to be overcome is that the therapy must destroy or inactivate the target tumour cells to a useful extent but that the therapy must not destroy or inactivate non-tumour cells to a deleterious extent. In other words, it is desirable if the therapy is selective for tumour cells to a beneficial extent.

Much of the current work on immunotherapy of cancer makes use of the fact that certain tumours express polypeptides which are not expressed in the equivalent non-tumour tissue, or makes use of the fact that the tumour expresses a mutant form of a polypeptide which is not expressed in the non-tumour tissue. However, it is not always possible to identify polypeptides in a tumour which fall into this category, and so other target polypeptides which can form the basis of an immunotherapeutic approach have been identified.

Work in melanoma patients has shown that peptide-epitopes recognised by melanoma-reactive CTL are frequently derived from tissue-specific differentiation antigens. Recognition of differentiation antigens which are expressed in normal tissues seems to violate the rules of immunological tolerance; however, the CTL recognition of melanoma-associated differentiation antigens could be explained by the fact that they are normally only expressed in melanocytes which exist in relative small numbers at immunologically privileged sites, thus failing to establish tolerance. There is also evidence that prostate-specific differentiation antigens can serve as targets for CTL against tumours of the prostate. To what extent developmentally regulated transcription factors can serve as targets for CTL against tumours aberrantly expressing these factors is currently unknown.

Gata-1 is a transcription factor which is normally expressed in the erythroid, megacaryocyte, eosinophil and mast cell lineages and in multipotential progenitors. Aberrant expression of this tightly controlled transcription factor is observed in leukaemia, including CML and AML (Shimamoto et al (1995) *Blood* 86, 3173-3180).

In adults, expression of WT1, an embryonic transcription factor, has been observed in renal podocytes, in the testis, in the ovary, in breast myoepithelial cells and in some CD34[+] stem cells in the bone marrow. Aberrant expression was observed in breast cancer, ovarian cancer, melanoma and leukaemia including CML and AML (see, for example, Menssen et al (1995) *Leukaemia* 9, 1060-1067; Inoue et al (1997) *Blood* 89, 1405-1412; Inoue et al (1996) *Blood* 88, 2267-2278; Inoue et al (1998) *Blood* 91, 2969-2976; Menssen et al (1997) *Int. J. Cancer* 70, 518-523; Menssen et al (1995) *Leukemia* 9, 1060-1067; Ogawa et al (1998) *Transplant* 21, 527—527; Rodeck et al (1994) *Int. J. Cancer* 59, 78-82; Silberstein et al (1997) *Proc. Natl. Acad. Sci. USA* 94, 8132-8137; Tamaki et al (1996) *Blood* 88, 4396-4398; and Viel et al (1994) *Int. J. Cancer* 57, 515-521).

U.S. Pat. No. 5,726,288 relates to the localisation and characterisation of the Wilms' tumour gene. Four amino acid sequences are disclosed (SEQ ID Nos 2, 4, 5 and 6) which contain either the sequence RMFPNAPYL (SEQ ID NO: 1) or CMTWMNQMNL, (SEQ ID NO: 2) but there is no disclosure of peptides corresponding to these sequences or of their use in immuno therapy.

Using an unconventional approach employing allo-MHC-restricted CTL, we have surprisingly identified peptide epitopes in the proteins WT-1 and gata-1 which may be presented by HLA-A0201 class I molecules and displayed on the surface of tumour cells expressing these proteins endogenously. HLA-A0201 negative responder individuals were used as a source of CTL specific for peptides presented by HLA-A0201 class I molecule, and this approach allows identification of HLA-A0201 presented peptides independent of possible tolerance of autologous CTL.

HLA-A0201 is the most common HLA-A haplotype.

For the avoidance of doubt, the terms HLA and MHC are used interchangeably in this specification.

A first aspect of the invention provides a peptide comprising the amino acid sequence RMFPNAPYL (SEQ ID NO: 1) or a portion or variant thereof provided that the peptide is not the intact human WT-1 polypeptide.

A second aspect of the invention provides a peptide comprising the amino acid sequence CMTWNQMNL (SEQ ID NO:2) or a portion or variant thereof provided that the peptide is not the intact human WT-1 polypeptide.

A third aspect of the invention provides a peptide comprising the amino acid sequence HLMPFPGPLL (SEQ ID NO: 3) or a portion or variant thereof provided that the peptide is not the intact human gata-1 polypeptide.

By "peptide" we include not only molecules in which amino acid residues are joined by peptide (—CO—NH—) linkages but also molecules in which the peptide bond is reversed. Such retro-inverso peptidomimetics may be made using methods known in the art, for example such as those described in Mézière et al (1997) *J. Immunol.* 159, 3230-3237, incorporated herein by reference. This approach involves making pseudopeptides containing changes involving the backbone, and not the orientation of side chains. Mézière et al (1997) show that, at least for MHC class II and T helper cell responses, these pseudopeptides are useful. Retro-inverse peptides, which contain NH—CO bonds instead of CO—NH peptide bonds, are much more resistant to proteolysis.

Similarly, the peptide bond may be dispensed with altogether provided that an appropriate linker moiety which retains the spacing between the Cα atoms of the amino acid residues is used; it is particularly preferred if the linker moiety has substantially the same charge distribution and substantially the same planarity of a peptide bond.

It will be appreciated that the peptide may conveniently be blocked at its N- or C-terminus so as to help reduce susceptibility to exoproteolytic digestion.

By a "portion" of the given amino acid sequence we mean at least six consecutive amino acids of the given sequence such that the peptide is still able to bind to an HLA molecule in substantially the same way as a peptide consisting of the given amino acid sequence.

By a "variant" of the given amino acid sequence we mean that the side chains of, for example, one or two of the amino acid residues are altered (for example by replacing them with the side chain of another naturally occurring amino acid residue or some other side chain) such that the peptide is still able to bind to an HLA molecule in substantially the same way as a peptide consisting of the given amino acid sequence. For example, a peptide may be modified so that it at least maintains, if not improves, the ability to interact with and bind a suitable MHC molecule, such as HLA-A0201, and so that it at least maintains, if not improves, the ability to generate activated CTL which can recognise and kill cells which aberrantly express a polypeptide which contains an amino acid sequence as defined in the first or second or third aspect of the invention (for example, WT1 or gata-1, as the case may be). Positions 2 and 9 of an HLA-A2-binding nonamer are typically anchor residues. Modifications of these and other residues involved in binding HLA-A2 may enhance binding without altering CTL recognition (for example, see Tourdot et al (1997) *J. Immunol.* 159, 2391-2398).

Those amino acid residues that are not essential to interact with the T cell receptor can be modified by replacement with another amino acid whose incorporation does not substantially effect T cell reactivity and does not eliminate binding to the relevant MHC.

Thus, apart from the proviso given, the peptide of the invention may be any peptide (by which term we include oligopeptide or polypeptide) which includes the amino acid sequences or a portion or variant thereof as given. Typically, the peptide of the invention is one which, if expressed in an antigen presenting cell, may be processed so that a fragment is produced which is able to bind to an appropriate MHC molecule and may be presented by a suitable cell and elicit a suitable T cell response. It will be appreciated that a fragment produced from the peptide may also be a peptide of the invention. Conveniently, the peptide of the invention contains a portion which includes the given amino acid sequence or a portion or variant thereof and a further portion which confers some desirable property. For example, the further portion may include a further T cell epitope (whether or not derived from the same polypeptide as the first T cell epitope-containing portion) or it may include a carrier protein or peptide. Thus, in one embodiment the peptide of the invention is a truncated human WT-1 protein or a fusion protein of a WT-1 protein fragment and another polypeptide portion provided that the human WT-1 portion includes the amino acid sequence RMFPNAPYL (SEQ ID NO: 1) or CMTWNQMNL (SEQ ID NO: 2) or both. In another embodiment the peptide of the invention is a truncated human gata-1 protein or a fusion protein of a human gata-1 protein fragment and another polypeptide portion provided that the human gata-1 portion includes the amino acid sequence HLMPFPGPLL (SEQ ID NO: 3).

In a particularly preferred embodiment, the peptide of the invention includes the amino acid sequence as given in the first, second or third aspect of the invention and at least one further T cell epitope wherein the further T cell epitope is able to facilitate the production of a T cell response directed at the type of tumour that aberrantly expresses WT-1 or gata-1. Thus, the peptides of the invention include so-called "beads on a string" polypeptides which can be used as vaccines.

The peptides of the invention may be of any size, but typically they may be less than 100 000 in molecular weight, preferably less than 50 000, more preferably less than 10 000 and typically about 5 000. In terms of the number of amino acid residues, the peptides of the invention may have fewer than 1000 residues, preferably fewer than 500 residues, more preferably fewer than 100 residues.

It will be appreciated from the following that in some applications the peptides of the invention may be used directly (ie they are not produced by expression of a polynucleotide in a patient's cell or in a cell given to a patient); in such applications it is preferred that the peptide has fewer than 100 residues.

It is preferred if the peptides of the invention are able to bind to HLA-A0201; however, the peptides may also bind to other HLA types as well as HLA-A0201. It is particularly preferred if the peptides bind selectively to HLA-A0201.

The peptides of the invention are particularly useful in immunotherapeutic methods to target and kill cells which aberrantly express the WT1 polypeptide (Wilms' tumour gene product) or the gata-1 polypeptide. The gata-1 polypeptide was so-named because it is a transcription factor which binds to a gata-box which is present in the promoter regions of some genes. It has also been called NF-e1, GF-1 and Eryf-1. The amino acid sequences RMFPNAPYL (SEQ ID NO: 1) and CMTWNQMNL (SEQ ID NO: 2) are found at residues 126-134 and 235-243, respectively, of WT1; the amino acid sequence HLMPFPGPLL (SEQ ID NO: 3) is found at residues 378-387 of gata-1. The WT-1 amino acid sequence is given in Gessler et al (1990) *Nature* 343, 774-778; and the gata-1 amino acid sequence is given in Zon et al (1990) *Proc. Natl. Acad. Sci. USA* 87, 668-672; both of these papers are incorporated herein by reference.

Since these specific peptides consisting of the given amino acid sequences bind to HLA-A0201 it is preferred that the peptides of the invention are ones which bind HLA-A0201 and when so bound the HLA-A0201-peptide complex, when present on the surface of a suitable antigen-presenting cell, is capable of eliciting the production of a CTL which recognises a cell which aberrantly expresses a polypeptide comprising the given amino acid sequence, such as the WT1 polypeptide with respect to the peptides of the first and second aspects of the invention, and such as the gata-1 polypeptide with respect to the peptides of the third aspect of the invention.

The WT1 polypeptide is aberrantly expressed in leukaemias, breast cancer, melanoma and ovarian cancer; the gata-1 polypeptide is aberrantly expressed in leukaemias.

By "aberrantly expressed" we include the meaning that the polypeptide is overexpressed compared to normal levels of expression or that the gene is silent in the tissue from which the tumour is derived but in the tumour it is expressed. By "overexpressed" we mean that the polypeptide is present at a level at least 1.2× that present in normal tissue; preferably at least 2× and more preferably at least 5× or 10× the level present in normal tissue.

It is well known that an optimum length for a peptide to bind to an HLA molecule is around 8 to 12 amino acid, preferably 9 amino acids.

Particularly preferred peptides of the invention are those consisting of the amino acid sequences RMFPNAPYL (SEQ ID NO: 1) or CMTWNQMNL (SEQ ID NO: 2) or HLMPFPGPLL (SEQ ID NO: 3).

If a peptide which is greater than around 12 amino acid residues is used directly to bind to a MHC molecule, it is preferred that the residues that flank the core HLA binding region are ones that do not substantially affect the ability of the peptide to bind to the MHC molecule or to present the peptide to the CTL. However, it will be appreciated that larger peptides may be used, especially when encoded by a polynucleotide, since these larger peptides may be fragmented by suitable antigen-presenting cells.

Peptides (at least those containing peptide linkages between amino acid residues) may be synthesised by the Fmoc-polyamide mode of solid-phase peptide synthesis as disclosed by Lu et al (1981) *J. Org. Chem.* 46, 3433 and references therein. Temporary N-amino group protection is afforded by the 9-fluorenylmethyloxycarbonyl (Fmoc) group. Repetitive cleavage of this highly base-labile protecting group is effected using 20% piperidine in N,N-dimethylformamide. Side-chain functionalities may be protected as their butyl ethers (in the case of serine threonine and tyrosine), butyl esters (in the case of glutamic acid and aspartic acid), butyloxycarbonyl derivative (in the case of lysine and histidine), trityl derivative (in the case of cysteine) and 4-methoxy-2,3,6-trimethylbenzenesulphonyl derivative (in the case of arginine). Where glutamine or asparagine are C-terminal residues, use is made of the 4,4'-dimethoxybenzhydryl group for protection of the side chain amido functionalities. The solid-phase support is based on a polydimethyl-acrylamide polymer constituted from the three monomers dimethylacrylamide (backbone-monomer), bisacryloylethylene diamine (cross linker) and acryloylsarcosine methyl ester (functionalising agent). The peptide-to-resin cleavable linked agent used is the acid-labile 4-hydroxymethyl-phenoxyacetic acid derivative. All amino acid derivatives are added as their preformed symmetrical anhydride derivatives with the exception of asparagine and glutamine, which are added using a reversed N,N-dicyclohexyl-carbodiimide/1-hydroxybenzotriazole mediated coupling procedure. All coupling and deprotection reactions are monitored using ninhydrin, trinitrobenzene sulphonic acid or isotin test procedures. Upon completion of synthesis, peptides are cleaved from the resin support with concomitant removal of side-chain protecting groups by treatment with 95% trifluoroacetic acid containing a 50% scavenger mix. Scavengers commonly used are ethanedithiol, phenol, anisole and water, the exact choice depending on the constituent amino acids of the peptide being synthesised. Trifluoroacetic acid is removed by evaporation in vacuo, with subsequent trituration with diethyl ether affording the crude peptide. Any scavengers present are removed by a simple extraction procedure which on lyophilisation of the aqueous phase affords the crude peptide free of scavengers. Reagents for peptide synthesis are generally available from Calbiochem-Novabiochem (UK) Ltd, Nottingham NG7 2QJ, UK. Purification may be effected by any one, or a combination of, techniques such as size exclusion chromatography, ion-exchange chromatography and (principally) reverse-phase high performance liquid chromatography. Analysis of peptides may be carried out using thin layer chromatography, reverse-phase high performance liquid chromatography, amino-acid analysis after acid hydrolysis and by fast atom bombardment (FAB) mass spectrometric analysis.

A further aspect of the invention provides a polynucleotide encoding a peptide as defined in the first or second or third aspects of the invention. The polynucleotide may be DNA or RNA and it may or may not contain introns so long as it codes for the peptide. Of course, it is only peptides which contain naturally occurring amino acid residues joined by naturally-occurring peptide bonds which are encodable by a polynucleotide.

A still further aspect of the invention provides an expression vector capable of expressing a polypeptide according to the first or second or third aspects of the invention.

A variety of methods have been developed to operably link polynucleotides, especially DNA, to vectors for example via complementary cohesive termini. For instance, complementary homopolymer tracts can be added to the DNA segment to be inserted to the vector DNA. The vector and DNA segment are then joined by hydrogen bonding between the complementary homopolymeric tails to form recombinant DNA molecules.

Synthetic linkers containing one or more restriction sites provide an alternative method of joining the DNA segment to vectors. The DNA segment, generated by endonuclease restriction digestion as described earlier, is treated with bacteriophage T4 DNA polymerase or *E. coli* DNA polymerase I, enzymes that remove protruding, 3'-single-stranded termini with their 3'-5'-exonucleolytic activities, and fill in recessed 3'-ends with their polymerizing activities.

The combination of these activities therefore generates blunt-ended DNA segments. The blunt-ended segments are then incubated with a large molar excess of linker molecules in the presence of an enzyme that is able to catalyze the ligation of blunt-ended DNA molecules, such as bacteriophage T4 DNA ligase. Thus, the products of the reaction are DNA segments carrying polymeric linker sequences at their ends. These DNA segments are then cleaved with the appropriate restriction enzyme and ligated to an expression vector that has been cleaved with an enzyme that produces termini compatible with those of the DNA segment.

Synthetic linkers containing a variety of restriction endonuclease sites are commercially available from a number of sources including International Biotechnologies Inc, New Haven, Conn., USA.

A desirable way to modify the DNA encoding the polypeptide of the invention is to use the polymerase chain reaction as disclosed by Saiki et al (1988) *Science* 239, 487-491. This method may be used for introducing the DNA into a suitable vector, for example by engineering in suitable restriction sites, or it may be used to modify the DNA in other useful ways as is known in the art.

In this method the DNA to be enzymatically amplified is flanked by two specific primers which themselves become incorporated into the amplified DNA. The said specific primers may contain restriction endonuclease recognition sites which can be used for cloning into expression vectors using methods known in the art.

The DNA (or in the case of retroviral vectors, RNA) is then expressed in a suitable host to produce a polypeptide comprising the compound of the invention. Thus, the DNA encoding the polypeptide constituting the compound of the invention may be used in accordance with known techniques, appropriately modified in view of the teachings contained herein, to construct an expression vector, which is then used to transform an appropriate host cell for the expression and production of the polypeptide of the invention. Such techniques include those disclosed in U.S. Pat. No. 4,440,859 issued 3 Apr. 1984 to Rutter et al, U.S. Pat. No. 4,530,901 issued 23 Jul. 1985 to Weissman, U.S. Pat. No. 4,582,800 issued 15 Apr. 1986 to Crowl, U.S. Pat. No. 4,677,063 issued 30 Jun. 1987 to Mark et al, U.S. Pat. No. 4,678,751 issued 7 Jul. 1987 to Goeddel, U.S. Pat. No. 4,704,362 issued 3 Nov. 1987 to Itakura et al, U.S. Pat. No. 4,710,463 issued 1 Dec. 1987 to Murray, U.S. Pat. No. 4,757,006 issued 12 Jul. 1988 to Toole, Jr. et al, U.S. Pat. No. 4,766,075 issued 23 Aug. 1988 to Goeddel et al and U.S. Pat. No. 4,810,648 issued 7 Mar. 1989 to Stalker, all of which are incorporated herein by reference.

The DNA (or in the case of retroviral vectors, RNA) encoding the polypeptide constituting the compound of the invention may be joined to a wide variety of other DNA sequences for introduction into an appropriate host. The companion DNA will depend upon the nature of the host, the manner of the introduction of the DNA into the host, and whether episomal maintenance or integration is desired.

Generally, the DNA is inserted into an expression vector, such as a plasmid, in proper orientation and correct reading frame for expression. If necessary the DNA may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a DNA sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant DNA of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example Saccharomyces cerevisiae), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith.

A promoter is an expression control element formed by a DNA sequence that permits binding of RNA polymerase and transcription to occur. Promoter sequences compatible with exemplary bacterial hosts are typically provided in plasmid vectors containing convenient restriction sites for insertion of a DNA segment of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (Ycps).

Other vectors and expression systems are well known in the art for use with a variety of host cells.

The present invention also relates to a host cell transformed with a polynucleotide vector construct of the present invention. The host cell can be either prokaryotic or eukaryotic. Bacterial cells may be preferred prokaryotic host cells in some circumstances and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Transformation of appropriate cell hosts with a DNA construct of the present invention is accomplished by well known methods that typically depend on the type of vector used. With regard to transformation of prokaryotic host cells, see, for example, Cohen et al (1972) *Proc. Natls. Acad. Sci. USA* 69, 2110 and Sambrook et al (1989) *Molecular Cloning, A Laboratory Manual*, Cold Spring Harbor Laboratory, Cold Spring Harbor, N.Y. Transformation of yeast cells is described in Sherman et al (1986) *Methods In Yeast Genetics, A Laboratory Manual*, Cold Spring Harbor, N.Y. The method of Beggs (1978) *Nature* 275, 104-109 is also useful. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells.

For example, many bacterial species may be transformed by the methods described in Luchansky et. al (1988) *Mol. Microbiol.* 2, 637-646 incorporated herein by reference. The greatest number of transformants is consistently recovered following electroporation of the DNA-cell mixture suspended in 2.5×PEB using 6250V per cm at 25 µFD.

Methods for transformation of yeast by electroporation are disclosed in Becker & Guarente (1990) *Methods Enzymol.* 194, 182.

Successfully transformed cells, ie cells that contain a DNA construct of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Southern (1975) *J. Mol. Biol.* 98, 503 or Berent et al (1985) *Biotech.* 3, 208. Alternatively, the presence of the protein in the supernatant can be detected using antibodies as described below.

In addition to directly assaying for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, in addition to the transformed host cells themselves, the present invention also contemplates a culture of those cells, preferably a monoclonal (clonally homogeneous) culture, or a culture derived from a monoclonal culture, in a nutrient medium.

It will be appreciated that certain host cells of the invention are useful in the preparation of the peptides of the invention, for example bacterial, yeast and insect cells. However, other host cells may be useful in certain therapeutic methods. For example, antigen-presenting cells, such as dendritic cells, may usefully be used to express the peptides of the invention such that they may be loaded into appropriate MHC molecules.

A further aspect of the invention provides a method of producing a peptide of the first or second or third aspect of the invention, the method comprising culturing host cells which contain a polynucleotide or expression vector which encodes the peptide and obtaining the peptide from the host cell or culture medium.

Further aspects of the invention provide pharmaceutical compositions which comprise a pharmaceutically acceptable carrier and a peptide according to the first, second or third aspects of the invention or a polynucleotide or expression vector encoding such a peptide. The pharmaceutical formulation is prepared in a form suitable for administration to a patient and is sterile and pyrogen free. Still further aspects of the invention provide a peptide according to any of the first or second or third aspects of the invention, or polynucleotides or expression vectors encoding such a peptide, for use in medicine. The peptides or polynucleotides or expression vectors are packaged and presented for use in medicine.

The pharmaceutical composition, or the package and presentation, may be in any suitable form. It is envisaged that suitable forms are for intravenous (i.v.) injection, subcutaneous (s.c.) injection, intradermal (i.d.) injection, intraperitoneal (i.p.) injection, intramuscular (i.m.) injection.

Preferred ways of peptide injection are s.c., i.d., i.p., i.m., and i.v.

Preferred ways of DNA injection are i.d., i.m., s.c., i.p. and i.v.

Doses of between 1 and 500 mg of peptide or DNA may be given.

A further aspect of the invention provides a method of killing target cells in a patient which target cells aberrantly express a polypeptide comprising an amino acid sequence of any of the first or second or third aspects of the invention, the method comprising administering to the patient an effective amount of a peptide according to any of the first or second or third aspects of the invention, or an effective amount of a polynucleotide or an expression vector encoding a said peptide, wherein the amount of said peptide or amount of said polynucleotide or expression vector is effective to provoke an anti-target cell immune response in said patient.

The target cell is typically a tumour or cancer cell. Typically the tumour or cancer cell is one which aberrantly expresses WT1 or gata-1.

The peptide or peptide-encoding nucleic acid constitutes a tumour or cancer vaccine. It may be administered directly into the patient, into the affected organ or systemically, or applied ex vivo to cells derived from the patient or a human cell line which are subsequently administered to the patient, or used in vitro to select a subpopulation from immune cells derived from the patient, which are then re-administered to the patient. If the nucleic acid is administered to cells in vitro, it may be useful for the cells to be transfected so as to co-express immune-stimulating cytokines, such as interleukin-2. The peptide may be substantially pure, or combined with an immune-stimulating adjuvant such as DETOX™, or used in combination with immune-stimulatory cytokines, or be administered with a suitable delivery system, for example liposomes. The peptide may also be conjugated to a suitable carrier such as keyhole limpet haemocyanin (KLH) or mannan (see WO 95118145 and Logenecker et al (1993) Ann. NY Acad. Sci., 690, 276-291). The peptide may also be tagged, or be a fusion protein, or be a hybrid molecule. The peptides whose sequence is given in the first or second or third aspects of the invention are expected to stimulate CD8 CTL. However, stimulation is more efficient in the presence of help provided by CD4 T cells. Thus, the fusion partner or sections of a hybrid molecule suitably provide epitopes which stimulate CD4 T cells. CD4 stimulating epitopes are well known in the art and include those identified in tetanus toxoid. The polynucleotide may be substantially pure, or contained in a suitable vector or delivery system. Suitable vectors and delivery systems include viral, such as systems based on adenovirus, vaccinia virus, retroviruses, herpes virus, adeno-associated virus or hybrids containing elements of more than one virus. Non-viral delivery systems include cationic lipids and cationic polymers as are well known in the art of DNA delivery. Physical delivery, such as via a "gene-gun" may also be used. The peptide or peptide encoded by the nucleic acid may be a fusion protein, for example with an epitope from tetanus toxoid which stimulates CD4 T cells.

The peptide for use in a cancer vaccine may be any suitable peptide. In particular, it may be a suitable 9-mer peptide or a suitable 7-mer or 8-mer or 10-mer peptide. Longer peptides may also be suitable, but 9-mer or 10-mer peptides are preferred. It may be advantageous, when the cancer vaccine is to be used in relation to WT1-expressing cancers if peptides of both the first and second aspects of the invention are used, or that a peptide is used which contains both of the sequences given in the first and second aspects of the invention.

Suitably, any nucleic acid administered to the patient is sterile and pyrogen free. Naked DNA may be given intramuscularly or intradermally or subcutaneously. The peptides may be given intramuscularly, intradermally or subcutaneously.

Vaccination results in CTL responses stimulated by professional antigen-presenting cells; once CTL are primed, there may be an advantage in enhancing MHC expression in tumour cells.

It may also be useful to target the vaccine to specific cell populations, for example antigen presenting cells, either by the site of injection, use of targeting vectors and delivery systems, or selective purification of such a cell population from the patient and ex vivo administration of the peptide or nucleic acid (for example dendritic cells may be sorted as described in Zhou et al (1995) *Blood* 86, 3295-3301; Roth et al (1996) *Scand. J. Immunology* 43, 646-651). For example, targeting vectors may comprise a tissue- or tumour-specific promoter which directs expression of the antigen at a suitable place.

Patients to whom the therapy is to be given, may have their tumours typed for overexpression or abnormal expression (both of which are aberrant expression) of WT1 or gata-1.

A further aspect of the invention therefore provides a vaccine effective against cancer, or cancer or tumour cells, comprising an effective amount of a peptide according to any one of the first or second or third aspects of the invention, or comprising a nucleic acid encoding such a peptide.

It is particularly preferred if the vaccine is a nucleic acid vaccine. It is known that inoculation with a nucleic acid vaccine, such as a DNA vaccine, encoding a polypeptide leads to a T cell response.

Conveniently, the nucleic acid vaccine may comprise any suitable nucleic acid delivery means. The nucleic acid, preferably DNA, may be naked (ie with substantially no other components to be administered) or it may be delivered in a liposome or as part of a viral vector delivery system.

It is believed that uptake of the nucleic acid and expression of the encoded polypeptide by dendritic cells may be the mechanism of priming of the immune response; however, dendritic cells may not be transfected but are still important since they may pick up expressed peptide from transfected cells in the tissue.

It is preferred if the vaccine, such as DNA vaccine, is administered into the muscle. It is also preferred if the vaccine is administered onto the skin.

The nucleic acid vaccine may be administered without adjuvant. The nucleic acid vaccine may also be administered with an adjuvant such as BCG or alum. Other suitable adjuvants include Aquila's QS21 STIMULON™ (Aquila Biotech, Worcester, Mass., USA) which is derived from saponin, mycobacterial extracts and synthetic bacterial cell wall mimics, and proprietory adjuvants such as Ribi's DETOX™. Quil A, another saponin-derived adjuvant, may also be used (Superfos, Denmark). It is preferred if the nucleic acid vaccine is administered without adjuvant.

Other adjuvants such as Freund's may also be useful. It may also be useful to give the peptide conjugated to keyhole limpet haemocyanin, preferably also with an adjuvant.

Polynucleotide-mediated immunization therapy of cancer is described in Conry et al (1996) *Seminars in Oncology* 23, 135-147; Condon et al (1996) *Nature Medicine* 2, 1122-1127; Gong et al (1997) *Nature Medicine* 3, 558-561; Zhai et al (1996) *J. Immunol.* 156, 700-710; Graham et al (1996) *Int J. Cancer* 65, 664-670; and Burchell et al (1996) pp 309-313 In: Breast Cancer, Advances in biology and therapeutics, Calvo et al (eds), John Libbey Eurotext, all of which are incorporated herein by reference.

A still further aspect of the present invention provides the use of a peptide according to the first or second or third aspect of the invention, or of a polynucleotide or expression vector encoding such a peptide, in the manufacture of a medicament for killing target cells in a patient which target cells aberrantly express a polypeptide comprising an amino acid sequence as defined in the first or second or third aspects of the invention.

Thus, the medicament is useful in treating cancers which aberrantly express WT1 or gata-1.

A further aspect of the invention provides a method for producing activated cytotoxic T lymphocytes (CTL) in vitro, the method comprising contacting in vitro CTL with antigen-loaded human class I MHC molecules expressed on the surface of a suitable antigen-presenting cell for a period of time sufficient to activate, in an antigen specific manner, said CTL wherein the antigen is a peptide according to any one of the first or second or third aspects of the invention.

Suitably, the CTL are CD8$^+$ cells but they may be CD4$^+$ cells. The MHC class I molecules may be expressed on the surface of any suitable cell and it is preferred if the cell is one which does not naturally express MHC class I molecules (in which case the cell is transfected to express such a molecule) or, if it does, it is defective in the antigen-processing or antigen-presenting pathways. In this way, it is possible for the cell expressing the MHC class I molecule to be primed substantially completely with a chosen peptide antigen before activating the CTL.

The antigen-presenting cell (or stimulator cell) typically has an MHC class I molecule on its surface and preferably is substantially incapable of itself loading said MHC class I molecule with the selected antigen. As is described in more detail below, the MHC class I molecule may readily be loaded with the selected antigen in vitro.

Conveniently, said antigen-presenting cell is a mammalian cell defective in the expression of a peptide transporter such that, when at least part of said selected molecule is a peptide, it is not loaded into said MHC class I molecule.

Preferably the mammalian cell lacks or has a reduced level or has reduced function of the TAP peptide transporter. Suitable cells which lack the TAP peptide transporter include T2, RMA-S and *Drosophila* cells. TAP is the Transporter Associated with antigen Processing.

Thus, conveniently the cell is an insect cell such as a *Drosophila* cell.

The human peptide loading deficient cell line T2 is available from the American Type Culture Collection, 12301 Parklawn Drive, Rockville, Md. 20852, USA under Catalogue No CRL 1992; the *Drosophila* cell line Schneider line 2 is available from the ATCC under Catalogue No CRL 19863; the mouse RMA-S cell line is described in Karre and Ljunggren (1985) *J. Exp. Med.* 162, 1745, incorporated herein by reference.

In a preferred embodiment the stimulator cell is a host cell (such as a T2, RMA-S or *Drosophila* cell) transfected with a nucleic acid molecule capable of expressing said MHC class I molecule. Although T2 and RMA-S cells do express before transfection HLA class I molecules they are not loaded with a peptide.

Mammalian cells can be transfected by methods well known in the art. *Drosophila* cells can be transfected, as described in Jackson et al (1992) *proc. Natl. Acad. Sci. USA* 89, 12117, incorporated herein by reference.

Conveniently said host cell before transfection expresses substantially no MHC class I molecules.

It is also preferred if the stimulator cell expresses a molecule important for T cell costimulation such as any of B7.1, B7.2, ICAM-1 and LFA 3.

The nucleic acid sequences of numerous MHC class I molecules, and of the costimulator molecules, are publicly available from the GenBank and EMBL databases.

It is particularly preferred if substantially all said MHC class I molecules expressed in the surface of said stimulator cell are of the same type.

HLA class I in humans, and equivalent systems in other animals, are genetically very complex. For example, there are at least 110 alleles of the HLA-B locus and at least 90 alleles of the HLA-A locus. Although any HLA class I (or equivalent) molecule is useful in this aspect of the invention, it is preferred if the stimulator cell presents at least part of the selected molecule in an HLA class I molecule which occurs at a reasonably high frequency in the human population. It is well known that the frequency of HLA class I alleles varies between different ethnic groupings such as Caucasian, African, Chinese and so on. At least as far as the Caucasian population is concerned it is preferred that HLA class I molecule is encoded by an HLA-A2 allele, or an HLA-A1 allele or an HLA-A3 allele or an HLA-B27 allele. HLA-A2 is particularly preferred.

In a further embodiment, combinations of HLA molecules may also be used. For example, a combination of HLA-A2 and HLA-A3 covers 74% of the Caucasian population.

The use of recombinant polyepitope vaccines for the delivery of multiple CD8 CTL epitopes is described in Thomson et al (1996) *J. Immunol.* 157, 822-826 and WO 96/03144, both of which are incorporated herein by reference. In relation to the present invention, it may be desirable to include in a single vaccine, a peptide (or a nucleic acid encoding a peptide) wherein the peptide includes, in any order, the amino acid sequence RMFPNAPYL, (SEQ ID NO: 1) CMTWNQMNL, (SEQ ID NO: 2) HLMPFPGPLL (SEQ ID NO: 3) and a CD4 T cell-stimulating epitope (such as from tetanus toxoid). Such a vaccine would be particularly useful for treating cancers which express WT-1 and gata-1. Such "bead-on-a-string" vaccines are typically DNA vaccines.

A convenient method of activating CTL (CD8+ cells) is described in WO 93/17095, incorporated herein by reference. The method of WO 93/17095 raises CTL against peptides presented by syngeneic (ie autologous) HLA class I molecules.

A number of other methods may be used for generating CTL in vitro. For example, the methods described in Peoples et al (1995) *Proc. Natl. Acad. Sci. USA* 92, 432-436 and Kawakami et al (1992) *J. Immunol.* 148, 638-643 use autologous tumour-infiltrating lymphocytes in the generation of CTL. Plebanski et al (1995) *Eur. J. Immunol.* 25, 1783-1787 makes use of autologous peripheral blood lymphocytes (PLBs) in the preparation of CTL. Jochmus et al (1997) *J. Gen. Virol.* 78, 1689-1695 describes the production of autologous CTL by employing pulsing dendritic cells with peptide or polypeptide, or via infection with recombinant virus.

Hill et al (1995) *J. Exp. Med.* 181, 2221-2228 and Jerome et al (1993) *J. Immunol.* 151, 1654-1662 make use of B cells in the production of autologous CTL. In addition, macrophages pulsed with peptide or polypeptide, or infected with recombinant virus, may be used in the preparation of autologous CTL.

Allogeneic cells may also be used in the preparation of CTL and this method is described in detail in WO 97/26328, incorporated herein by reference. For example, in addition to *Drosophila* cells and T2 cells, other cells may be used to present antigens such as CHO cells, baculovirus-infected insects cells, bacteria, yeast, vaccinia-infected target cells. In addition plant viruses may be used (see, for example, Porta et al (1994) *Virology* 202, 449-955 which describes the development of cowpea mosaic virus as a high-yielding system for the presentation of foreign peptides.

It is preferred if allogeneic cells are used in the preparation of CTL so that the CTL are allo-MHC-restricted with respect to the peptides of the invention. It is particularly preferred that the CTL are from a HLA-A0201 negative responder individual and that the peptide is presented by a HLA-A0201 class I molecule by the antigen-presenting cell.

Exogenously applied peptides may be linked to a HIV tat peptide to direct them into the MHC Class I pathway for presentation by CTL (see, for example, Kim et al (1997) *J. Immunol.* 159, 1666-1668.

The activated CTL which are directed against the peptides of the invention are useful in therapy. Thus, a further aspect of the invention provides activated CTL obtainable by the foregoing methods of the invention.

A still further aspect of the invention provides activated CTL which selectively recognise a cell which aberrantly expresses a polypeptide comprising an amino acid sequence given in any of the first or second or third aspects of the invention. Preferably, the CTL recognises the said cell by binding to the peptide as defined in any of the first or second or third aspects of the invention.

The CTL are useful in a method of killing target cells in a patient which target cells aberrantly express a polypeptide comprising an amino acid sequence given in any one of the first or second or third aspects of the invention wherein the patient is administered an effective number of the activated CTL.

The CTL which are administered to the patient may be derived from the patient and activated as described above (ie they are autologous CTL). Alternatively, the CTL are not from the patient but are from another individual. Of course, it is preferred if the individual is a healthy individual. By "healthy individual" we mean that the individual is generally in good health, preferably has a competent immune system and, more preferably, is not suffering from any disease which can be readily tested for, and detected. In this embodiment, the CTL are derived from an individual whose HLA class I molecules are mismatched with those of the patient. Thus, it is preferred if the CTL are allo-restricted. Treatment with allo-restricted CTL is described in my earlier patent application WO 97/26328, incorporated herein by reference.

Thus, the methods of the invention include methods of adoptive immunotherapy.

The activated CTL contain a T cell receptor (TCR) which is involved in recognising cells which express the aberrant polypeptide. It is useful if the cDNA encoding the TCR is cloned from the activated CTL and transferred into a further CTL for expression.

The TCRs of CTL clones of the invention (whether allo-restricted or self-restricted) specific for the peptides of the first or second or third aspects of the invention are cloned. The TCR usage in the CTL clones is determined using (i) TCR variable region-specific monoclonal antibodies and (ii) RT-PCR with primers specific for Vα and Vβ gene families. A cDNA library is prepared from poly-A mRNA extracted from the CTL clones. Primers specific for the C-terminal portion of the TCR α and β chains and for the N-terminal portion of the identified Vα and β segments are used. The complete cDNA for the TCR α and β chain is amplified with a high fidelity DNA polymerase and the amplified products cloned into a suitable cloning vector. The cloned α and β chain genes may be assembled into a single chain TCR by the method as described by Chung et al (1994) *Proc. Natl. Acad. Sci. USA* 91, 12654-12658. In this single chain construct the VαJ segment is followed by the VβDJ segment, followed by the Cβ segment followed by the transmembrane and cytoplasmic segment of the CD3 ζ (chain. This single chain TCR is then inserted into a retroviral expression vector (a panel of vectors may be used based on their ability to infect mature human CD8+ T lymphocytes and to mediate gene expression: the retroviral vector system Kat is one preferred possibility (see Finer et al (1994) *Blood* 83, 43). High titre amphotrophic retrovirus are used to infect purified CD8+ T lymphocytes isolated from the peripheral blood of tumour patients following a protocol published by Roberts et al (1994) *Blood* 84, 2878-2889, incorporated herein by reference. Anti-CD3 antibodies are used to trigger proliferation of purified CD8+ T cells, which facilitates retroviral integration and stable expression of single chain TCRs. The efficiency of retroviral transduction is determined by staining of infected CD8+ T cells with antibodies specific for the single chain TCR. In vitro analysis of transduced CD8+ T cells establishes that they display the same tumour-specific killing as seen with the allo-restricted CTL clone from which the TCR chains were originally cloned. Populations of transduced CD8+ T cells with the expected specificity may be used for adoptive immunotherapy of the tumour patients. Patients may be treated with in between $10^8$ to $10^{11}$ (most likely $10^9$-$10^{10}$) autologous, transduced CTL.

Other suitable systems for introducing genes into CTL are described in Moritz et al (1994) *Proc. Natl. Acad. Sci. USA* 91, 4318-4322, incorporated herein by reference. Eshhar et al (1993) *Proc. Natl. Acad. Sci. USA* 90, 720-724 and Hwu et al (1993) *J. Exp. Med.* 178, 361-366 also describe the transfection of CTL.

Thus, a further aspect of the invention provides a TCR which recognises a cell which aberrantly expresses a polypeptide comprising an amino acid sequence given in any one of the first or second or third aspects of the invention, the TCR being obtainable from the activated CTL.

As well as the TCR, functionally equivalent molecules to the TCR are included in the invention. These include any molecule which is functionally equivalent to a TCR which can perform the same function as a TCR. In particular, such molecules include genetically engineered three-domain single-chain TCRs as made by the method described by Chung et al (1994) *Proc. Natl. Acad. Sci. USA* 91, 12654-12658, incorporated herein by reference, and referred to above.

The invention also includes a polynucleotide encoding the TCR or functionally equivalent molecule, and an expression vector encoding the TCR or functionally equivalent molecule thereof. Expression vectors which are suitable for expressing the TCR of the invention include those described above in respect of expression of the peptides of the invention. It is, however, preferred that the expression vectors are ones which are able to express the TCR in a CTL following transfection.

A still further aspect of the invention provides a method of killing target cells in a patient which target cells aberrantly express a polypeptide comprising an amino acid sequence given in any of the first or second or third aspects of the invention, the method comprising the steps of (1) obtaining CTL from the patient; (2) introducing into said cells a polynucleotide encoding a TCR, or a functionally equivalent molecule, as defined above; and (3) introducing the cells produced in step (2) into the patient.

A still further aspect of the invention provides a method of killing target cells in a patient which target cells aberrantly express a polypeptide comprising an amino acid sequence as defined in the first or second or third aspects of the invention, the method comprising the steps of (1) obtaining antigen presenting cells, such as dendritic cells, from said patient; (2) contacting said antigen presenting cells with a peptide as defined in the first or second or third aspects of the invention, or with a polynucleotide encoding such a peptide, ex vivo; and (3) reintroducing the so treated antigen presenting cells into the patient.

Preferably, the antigen presenting cells are dendritic cells.

Suitably, the dendritic cells are autologous dendritic cells which are pulsed with an antigenic peptide. The antigenic peptide may be any suitable antigenic peptide which gives rise to an appropriate T cell response. T-cell therapy using autologous dendritic cells pulsed with peptides from a tumour associated antigen is disclosed in Murphy et al (1996) *The Prostate* 29, 371-380 and Tjua et al (1997) *The Prostate* 32, 272-278.

In a further embodiment the antigen presenting cells, such as dendritic cells, are contacted with a polynucleotide which encodes a peptide of the invention. The polynucleotide may be any suitable polynucleotide and it is preferred that it is capable of transducing the dendritic cell thus resulting in the presentation of a peptide and induction of immunity.

Conveniently, the polynucleotide may be comprised in a viral polynucleotide or virus. For example, adenovirus-transduced dendritic cells have been shown to induce antigen-specific antitumour immunity in relation to MUC1 (see Gong et al (1997) *Gene Ther.* 4, 1023-1028). Similarly, adenovirus-based systems may be used (see, for example, Wan et al (1997) *Hum. Gene Ther.* 8, 1355-1363); retroviral systems may be used (Specht et al (1997) *J. Exp. Med.* 186, 1213-1221 and Szabolcs et al (1997) *Blood* 90, 2160-2167); particle-mediated transfer to dendritic cells may also be used (Tuting et al (1997) *Eur. J. Immunol.* 27, 2702-2707); and RNA may also be used (Ashley et al (1997) *J. Exp. Med.* 186, 1177-1182).

It will be appreciated that, with respect to the methods of killing target cells in a patient, it is particularly preferred that the target cells are cancer cells.

The WT1 polypeptide comprises the amino acid sequences RMFPNA PYL (SEQ ID NO: 1) and CMTWNQMNL, (SEQ ID NO: 2) and it is aberrantly expressed in leukaemias, breast cancer, melanoma and ovarian cancer.

The gata-1 polypeptide comprises the amino acid sequence HLMPFPGPLL, (SEQ ID NO: 3) and it is aberrantly expressed in leukaemias.

It is particularly preferred if the patients who are treated by the methods of the invention have the HLA-A0201 haplotype. Thus, in a preferred embodiment the HLA haplotype of the patient is determined prior to treatment. HLA haplotyping may be carried out using any suitable method; such methods are well known in the art.

The invention includes in particular the use of the peptides of the invention (or polynucleotides encoding them) for active in vivo vaccination; for manipulation of autologous dendritic cells in vitro followed by introduction of the so-manipulated dendritic cells in vivo to activate CTL responses; to activate autologous CTL in vitro followed by adoptive therapy (ie the so-manipulated CTL are introduced into the patient); and to activate CTL from healthy donors (MHC matched or mismatched) in vitro followed by adoptive therapy.

The invention will now be described in more detail by reference to the following Figures and Examples in which:

FIG. 1 shows the killing activity of anti-WT126-34 CTL. T2 is a human cell line with a peptide-loading defect which is available from the ATCC under Catalogue No CRL 1992. They are loaded with the WT126-34 peptide (RMFPNAPYL; SEQ ID NO: 1) (T2+ WT12) or with E7 control peptide (TLGIVCPI; SEQ ID NO: 4) which is an irrelevant HLA-A2-binding peptide (T2+ E7).

K562 is a leukaemia cell line and K562-A2 is the K562 leukaemia cell line transfected with HLA-A0201. The E:T ratio is the effector: target cell ratio. Specific lysis (%) is measured in a standard CTL assay such as that described in Sadovnikova & Stauss (1996) *Proc. Natl. Acad. Sci. USA* 93, 13114-13118, incorporated herein by reference.

Figure 2:
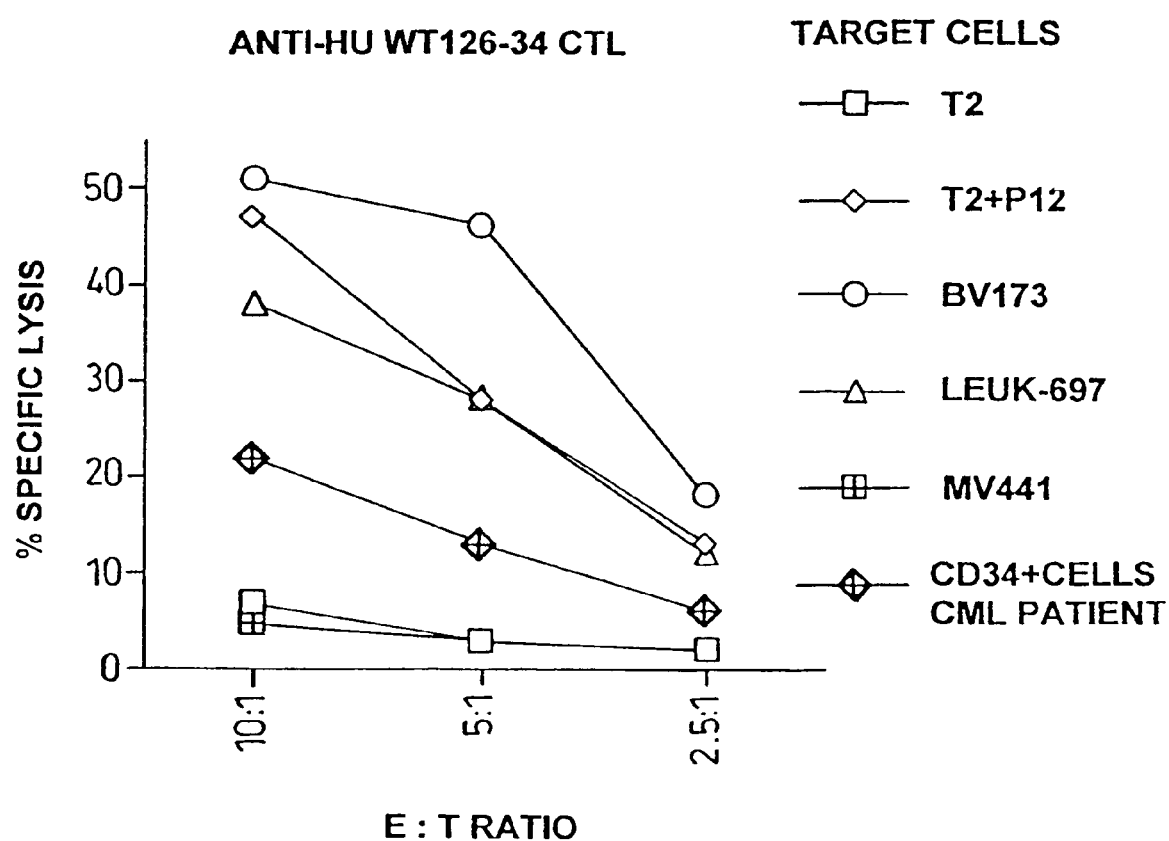

FIG. 2 shows the killing activity of anti-huWT126-34 CTL. Leuk-697, MV441 and BV173 are leukaemia cell lines. P12 stands for WT126-34 peptide (RMFPNAPYL; SEQ ID NO: 1).

Figure 3:
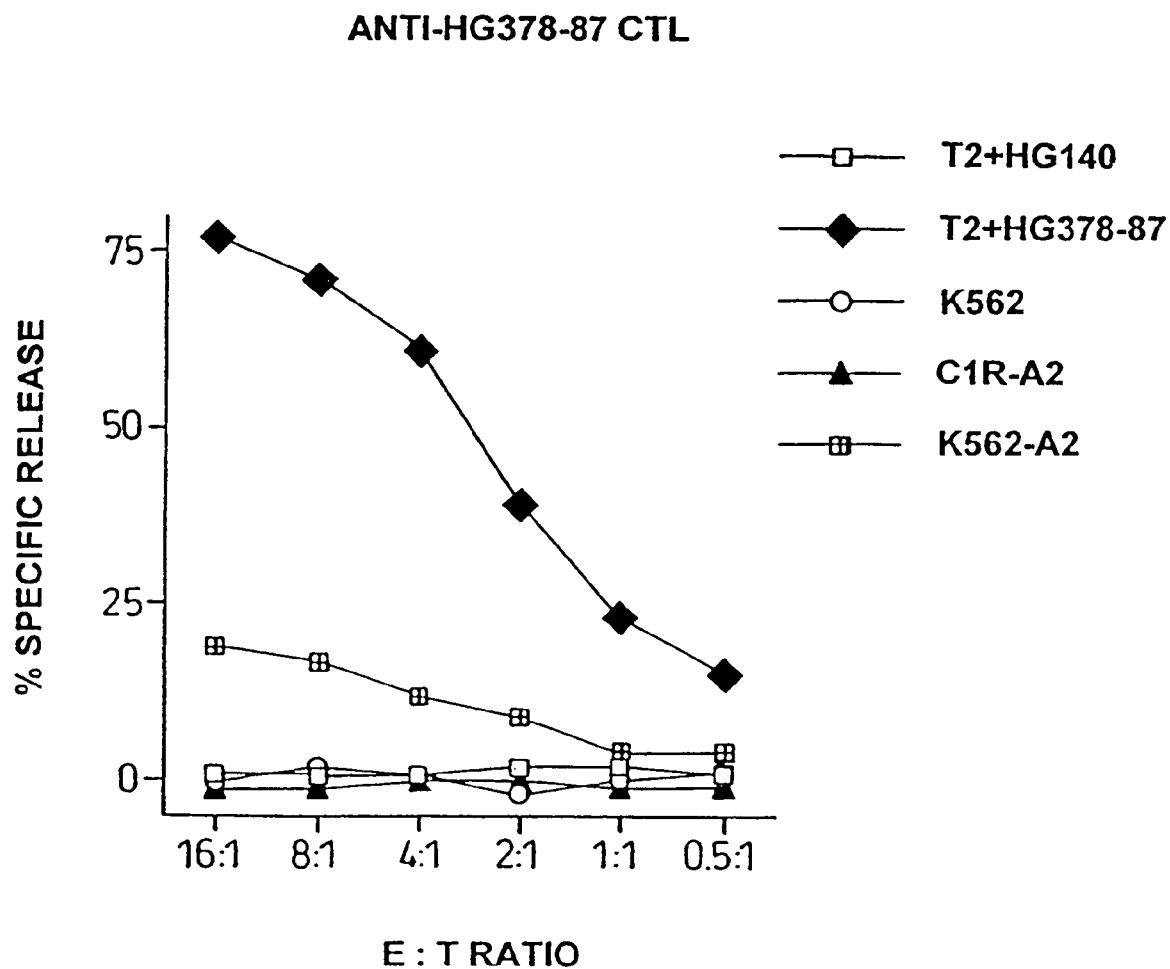

FIG. 3 shows the killing activity of an anti-hug 378-87 CTL. hug 378-87 is the peptide HLMPFPGPLL (SEQ ID NO: 3) and hug 14 is an HLA-A2-binding control peptide (RLSPDLLTL; SEQ ID NO: 5). C1R-A2 is a human B-lymphoid cell line. K562-A2 human is a leukaemia cell line.

FIG. 4 shows the specificity of allo-restricted CTL generated against the WT1-derived peptide P126. CTL were isolated by limiting dilution cloning of T lymphocyte bulk cultures from HLA-A0201⁻ donors stimulated with HLA-A0201⁺ stimulator cells coated with P126 peptide. (A) Isolated CTL lines killed the TAP-deficient T2 target cells coated with the immunising P126 peptide but not T2 cells coated with the HLA-A0201-binding E7 control peptide. (B) Peptide titration experiments showing that 3 anti-P126 CTL lines were of high avidity recognising low picomolar concentration of P126, and 3 CTL lines were of low avidity since nanomaler P126 concentration were required for target cell recognition. T2 cells coated with the indicated concentrations of P126 were used as CTL targets. High avidity CTL were used for all subsequent experiments because low avidity CTL did not recognise target cells expressing WT1 endogenously. (C) High avidity CTL kill the HLA-A0201⁺ leukemic cell lines BV173, 697 but not the HLA-A0201⁺, EBV-transformed B-lymphoid cells C1R-A2. Coating of C1R-A2 with P126 resulted in efficient CTL killing. The HLA-A0201⁻ leukemia cell line K562 is not killed by the CTL unless transfected with the HLA-A0201 gene.

Figure 4C:
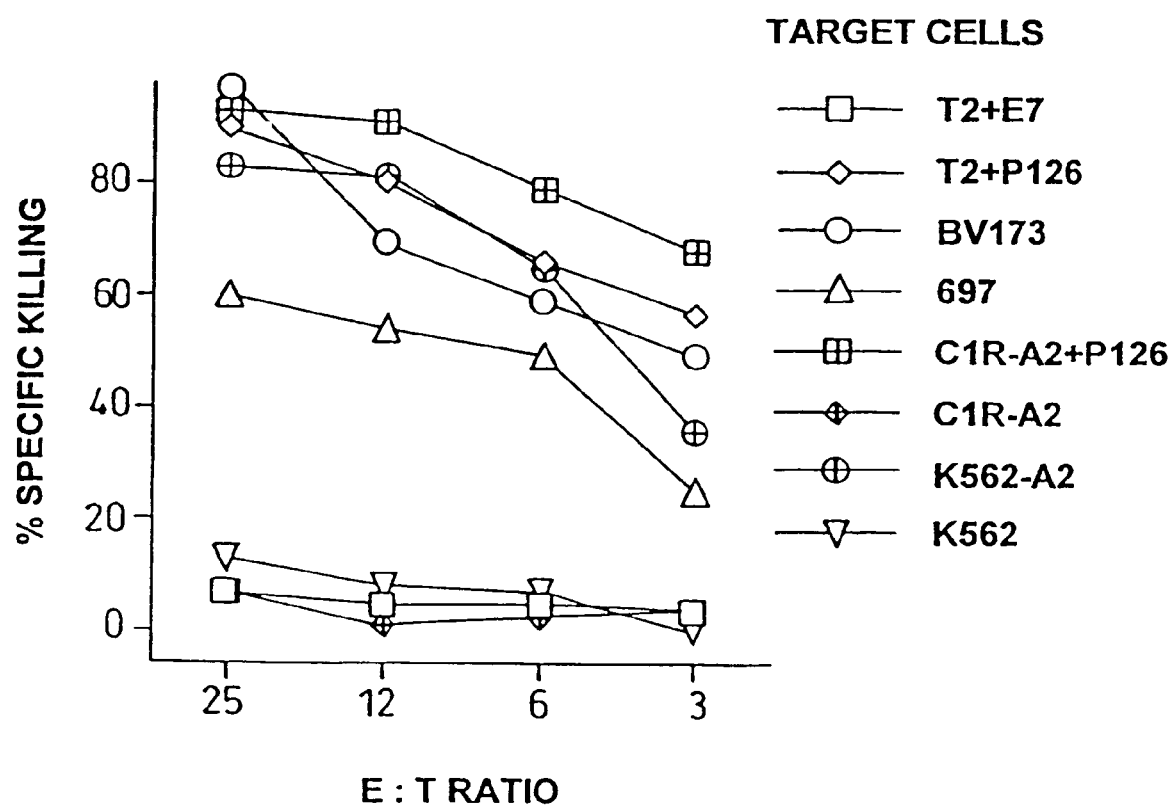
Figure 5:
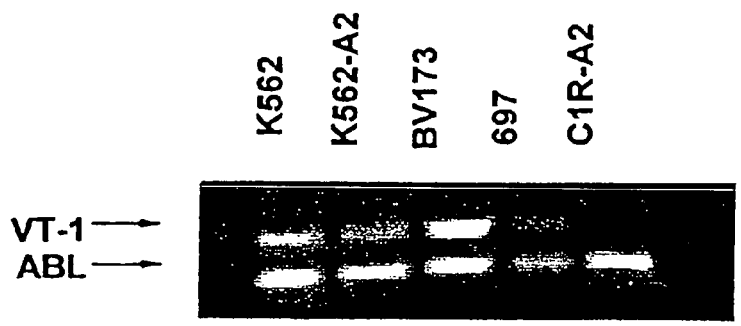
Figure 5:
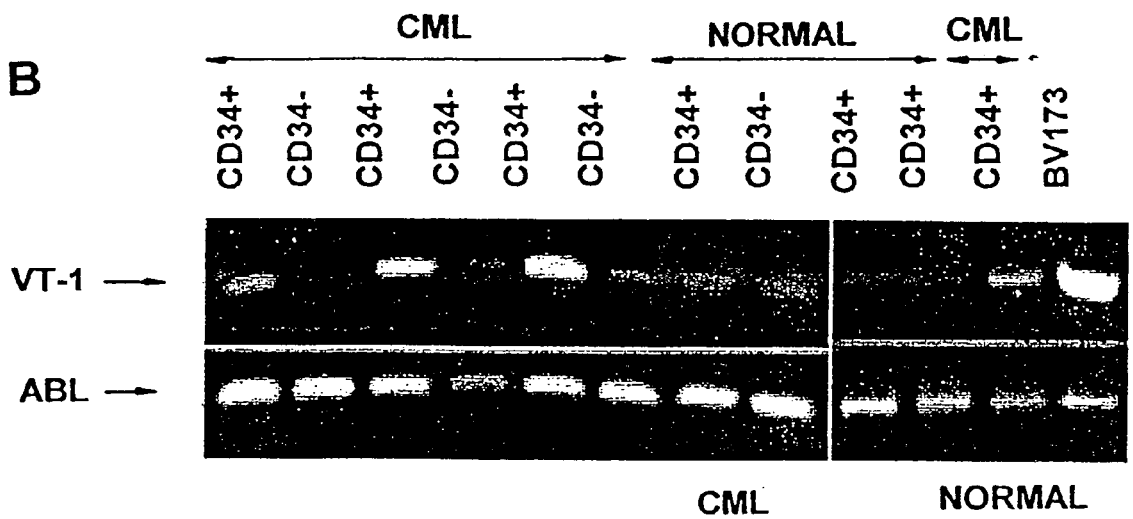
Figure 5:
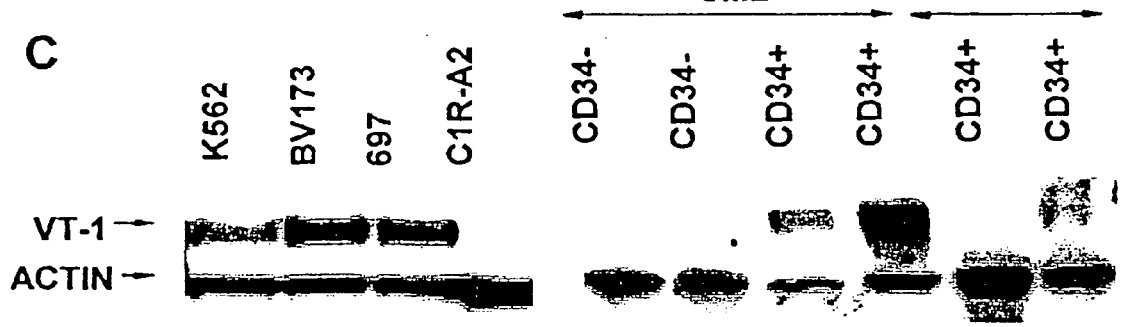

FIG. 5 shows WT1 RNA and protein expression in leukemic cell lines and in CD34⁺ and CD34⁻ cell populations freshly isolated from leukemia patients and normal donors. (A) RT-PCR to measure WT1 RNA in leukemic cell lines and in the B-lymphoid cell line C1R-A2. The same cell lines were used as CTL targets in FIG. 4C. The amplified WT1 product is 482 bp, The RNA of the house keeping ABL gene was amplified to indicate the amount of RNA in each sample. The ABL product is 385 bp long. (B) RT-PCR to measure WT1 RNA expression in purified CD34⁺ and CD34⁻ cell populations from 4 CML patients and 3 normal donors. The leukemic cell line BV173 served as positive control for WT1 expression. Similar results were obtained with samples from additional 6 CML patients. (C) Western blotting to measure WT1 protein expression in leukemia cell lines and in purified CD34⁺ and CD34⁻ cell populations from 2 CML patients and 2 normal donors. The expression of the house keeping actin protein was used as indicator to control for the amount of protein present in each sample. The WT1 protein in approximately 54 kDa in size and the actin protein approximately 42 kDa.

FIG. 6 is an analysis of CTL-mediated killing and inhibition of colony formation of CD34⁺ cell populations purified from leukemic patients and normal donors. (A) Representative experiment showing the level of killing by anti-P126 CTL against purified CD34⁺ and CD34⁻ cell populations isolated from CML patients who were either HLA-A0201⁺ or A0201⁻. CD34⁻/A0201⁺ cells were not recognised by the CTL unless coated with P126 peptide. The leukemic cell line BV173 and the TAP-deficient T2 cells coated with P126 or the control E7 peptide were used as positive and negative controls in all experiments. (B) Average of the level of specific CTL killing of purified CD34⁺ cells from 11 different HLA-A0201⁺ CML patients and from 6 normal donors. The level of killing of CD34⁻ cells purified from CML patients and against the positive control cells BV173 is also shown. The figure shows the mean level and standard deviation of specific CTL killing. (C) Representative experiment showing the level of killing by anti-P126 CTL of purified CD34⁺ and CD34⁻ cell populations isolated from HLA-A0201⁺ normal donors. No CTL killing was detectable unless target cells were coated with P126 peptide. (D) CTL-mediated inhibition of colony formation by purified CD34⁺ cells co-cultured for 4 hours with CTL at an effector/target cell ratio of 10:1. Untreated control CD34⁺ cells were cultured under the same conditions without CTL. CTL treated and untreated control cells were then plated in methylcellulose and after 14 days the numbers of CFU-GM were counted. Shown is the percentage of CFU-GM after CTL treatment using the CFU-GM observed in the untreated controls as 100% reference. The figure shows the mean and standard deviation of independent experiments with CD34⁺ cells from 9 different HLA-A0201⁺ CML patients, 7 different normal donors, and with CD34⁺ cells from 5 different HLA-A0201⁻ CML patients. (E) Colony formation by A0201⁺ CD34⁺ CML cells that were untreated or treated for 4 hours with high avidity P126-specific CTL (line 81) or with low avidity CTL (line 85) prior to plating. Shown are CFU-GM and BFU-E using the number of colonies observed in the untreated controls as 100% reference. (F) Cold target competition experiment. Shown is the killing by anti-P126 CTL against chromium-labelled CD34⁺ targets from a A0201⁺ CML patient in the absence or presence of a 30 fold excess of cold BV173 and C1R-A2 targets. The killing of chromium-labelled BV173 and C1R-A2 is shown for comparison.

EXAMPLE 1

The Identification of HLA-A0201 Presented CTL Epitopes in WT-1 and gata-1

Eight WT-1 peptides with HLA-A2 binding motifs were analysed and two were found to be natural CTL epitopes. Twelve gata-1 peptides with HLA-A2 binding motifs were analysed and one was found to be a natural CTL epitope.

The following approach was used: i) analysis of synthetic peptides in HLA-A0201 binding assays; iii) use of HLA-A0201 binding peptides to stimulate CTL responses from HLA-A0201 negative individuals; iv) test of peptide-specific CTL against tumour cells expressing WT-1 or gata-1 endogenously.

Peptide binding assay: $5 \times 10^5$ T2 cells were incubated overnight (o/n) in 96 well plates in 100 ml of RPMI 1640 medium with 5% boiled FCS (to destroy proteases) and varying concentrations of synthetic peptides. Wells containing T2 cells without peptides or known A2-binding peptides were used as negative and positive control, respectively. Following overnight incubation cells were washed and stained by indirect immunofluorescence for surface HLA-A2 with A-2 specific monoclonal antibodies HB54 and HB117 (American Type Culture Collection, ATCC). FACS analysis was performed on a Coulter Corporation flow cytometer (Haiteah, Fla.).

Generation of allo-restricted CTL lines and clones: PBMC from HLA-A2 negative buffy coat blood packs were used as responders. Each well of a 24 well plate received $2 \times 10^6$ Ficoll separated PBMC and $2 \times 10^5$ stimulator cells. Stimulator cells were prepared by overnight incubation of T2 cells in 100 μM peptide in RPMI with 5% boiled FCS. On day 5 T cells were harvested and plated in fresh T cell medium at a density of $5 \times 10^5$ per well in a 24 well plate with the addition of $2 \times 10^6$ autologous irradiated PBMC as feeders, $2 \times 10^5$ peptide coated irradiated T2 or C1R-A2 cells, 500 nM peptide and 10% QS4120 culture supernatant to suppress outgrowth of CD4 T cells. The cultures were fed every 2 weeks using HLA-A2 positive cell lines coated with the immunising peptide as stimulators. The bulk cultures were cloned in T cell medium at a density of 1, 10 and 30 cells per well. $10^4$ peptide-coated T2 cells, $2\times10^5$ HLA-A2 negative feeders and 2 U IL-2 were added to each well. CTL obtained from microcultures seeded at 1 cell per well are further referred to as clones if the percentage of wells growing cells did not exceed 30%.

CTL assays: $10^6$ T2 cells were incubated for 1 hr in 200 μl of assay medium (RPMI 1640 with 5% heat inactivated FCS) with 100 μM synthetic peptide at 37° C. Peptide coated and uncoated cells were $^{51}$Cr-labelled for an additional hour, washed and added to serial two-fold dilutions of effector cells in round bottom 96 well plates to obtain a total volume of 200 μl/well. CTL bulk lines were analysed in the presence of 30 cold K562 cells per $^{51}$Cr-labelled target cell to reduce the background killing caused by NK cells. To test the sensitivity of T cell clones serial dilutions of peptides in assay medium were made in 96 well plates. $5\times10^3$ $^{51}$Cr-labelled T2 cells were added to each well to obtain a total volume of 100 μl and incubated for 1 hr. Effector cells were added at an E:T ratio sufficient for maximal CTL killing. Assay plates were incubated at 37° C., 5% $CO_2$ and after 4 h 100 μl of supernatant was harvested from each well and counted using a Wallac Gamma Counter. The specific lysis was calculated by the equation (experimental release−spontaneous release)/(maximum release−spontaneous release)× 100%.

RESULTS

In the WT-1 protein two CTL recognised peptide epitopes expressed in WT-1 expressing tumour cells were identified:
WT126-34:RMFPNAPYL (SEQ ID NO:1)
WT235-43:CMTWNQMNL (SEQ ID NO:2)

These are 9 amino acid long peptides and are likely to represent the minimal epitope required for efficient recognition by CTL.

The killing activity of CTL against the WT126-34 is shown in the following table:

| Target cell | HLA-A0201 expression | WT-1 expression | Killing by anti-WT126-34 CTL |
|---|---|---|---|
| leukaemia cell line BV173 | yes | yes | yes |
| leukaemia cell line Leuk-697 | yes | yes | yes |
| leukaemia cell line MV441 | no | yes | no |
| leukaemia cell line K562 | no | yes | no |
| leukaemia cell line K562 transfected with HLA-A0201 | yes | yes | yes |
| freshly isolated CD34+ leukamic cells from A0201-positive patients | yes | yes | yes |
| freshly isolated CD34+ leukaemic cells from A0201-negative patients | no | yes | no |
| breast cancer cell line MDA-MB231 | yes | yes | yes |
| C1R-A2 cell line | yes | no | no |
| EBV transformed cells from A0201-positive patients | yes | no | no |

The data in the table illustrate that CTL against the WT126-34 peptide kill tumour cells expressing WT-1 and HLA-A0201. WT-1 negative B lymphoblastoid cells are not killed. FIGS. 1 and 2 show representative experiments illustrating the killing activity of anti-WT126-34 CTL.

The data set obtained with anti-WT235-43 CTL is not as extensive as the data obtained with WT126-34 CTL. It is clear, however, that anti-WT235-43 CTL kill HLA-A0201-positive tumour cells expressing WT-1 endogenously.

In the gata-1 protein one CTL recognised peptide epitopes expressed in gata-1 expressing tumour cells was identified:
Hug-378-87 HLMPFPGPLL (SEQ ID NO:3).

This is a 10 amino acid long peptides and are likely to represent the minimal epitope required for efficient recognition by CTL.

CTL against this peptide can recognise the HLA-A0201 transfected K562 leukaemia cell line expressing gata-1 endogenously, while untransfected K562 cells are not recognised.

CONCLUSION

CTL recognised peptide epitopes in WT-1 and gata-1 have been identified. These epitopes are displayed on tumour cells aberrantly expressing these proteins. The physiological expression of WT-1 and gata-1 is limited to a relatively small number of normal cells. Thus, it is possible that autologous CTL show limited tolerance to these proteins and that the identified CTL epitopes can be used for vaccination against tumours with aberrant WT-1 and gata-1 expression, respectively, and in other immunotherapeutic methods.

EXAMPLE 2

Production of Activated Cytotoxic Lymphocytes (CTL) Using Class I Molecules and the WT-1 Peptide Antigen RMFPNAPYL (SEQ ID NO: 1) and their Administration Activated cytotoxic T lymphocytes (CTLs) are produced using HLA-A2 Class I molecules and the nonamer peptide from WT1: RMFPNAPYL (SEQ ID NO: 1).

The method described in PCT patent application WO 93/17095 is used to make the CTLs. *Drosophila* cells are used to present the peptide antigen to CTL. The HLA-A2 molecule is expressed in the *Drosophila* cells.

The peptide is synthesised on an Applied Biosystems synthesiser, ABI 431A (Foster City, Calif., USA) and subsequently purified by HPLC.

As is described in detail in WO 93/17095, in order to optimize the in vitro conditions for the generation of specific cytotoxic T cells, the culture of stimulator cells is maintained in an appropriate medium. The stimulator cells are *Drosophila* cells as described in WO 93/17095, which are preferably maintained in serum-free medium (eg Excell 400).

Prior to incubation of the stimulator cells with the cells to be activated, eg precursor CD8 cells, an amount of antigenic peptide is added to the stimulator cell culture, of sufficient quantity to become loaded onto the human Class I molecules to be expressed on the surface of the stimulator cells. A sufficient amount of peptide is an amount that will allow about 200, and preferably 200 or more, human Class I MHC molecules loaded with peptide to be expressed on the surface of each stimulator cell. The stimulator cells are typically incubated with >20 μg/ml peptide.

Resting or precursor CD8 cells are then incubated in culture with the appropriate stimulator cells for a time period sufficient to activate the CD8 cells. The CD8 cells shall thus be activated in an antigen-specific manner. The ratio of resting or precursor CD8 (effector) cells to stimulator cells may vary from individual to individual and may further depend upon variables such as the amenability of an individual's lymphocytes to culturing conditions. The lymphocyte:stimulator cell (*Drosophila* cell) ratio is typically in the range of about 30:1 to 300:1. For example, $3 \times 10^7$ human-PBL and $1 \times 10^6$ live *Drosophila* cells are admixed and maintained in 20 ml of RPMI 1640 culture medium.

The effector/stimulator culture are maintained for as long a time as is necessary to stimulate a therapeutically usable or effective number of CD8 cells. The optimum time is typically between about one and five days, with a "plateau", ie a "maximum" specific CD8 activation level, generally being observed after five days of culture. In vitro activation of CD8 cells is typically detected within a brief period of time after transfection of a cell line. Transient expression in a transfected cell line capable of activating CD8 cells is detectable within 48 hours of transfection. This clearly indicates that either stable or transient cultures of transformed cells expressing human Class I MHC molecules are effective in activating CD8 cells.

Activated CD8 cells may be effectively separated from the stimulator (*Drosophila*) cells using monoclonal antibodies specific for the stimulator cells, for the peptides loaded onto the stimulator cells, or for the CD8 cells (or a segment thereof) to bind their appropriate complementary ligand. Antibody-tagged molecules are then extracted from the stimulator-effector cell admixture via immunoprecipitation or immunoassay methods.

Effective, cytotoxic amounts of the activated CD8 cells can vary between in vitro and in vivo uses, as well as with the amount and type of cells that are the ultimate target of these killer cells between about $1 \times 10^6$ and $1 \times 10^{12}$ activated CTL are used for adult humans.

The activated CD8 cells are harvested from the *Drosophila* cell culture prior to administration of the CD8 cells to the individual being treated. It is important to note, however, that unlike other present and proposed treatment modalities, the method described in this Example uses a cell culture system (ie *Drosophila* cells) that are not tumorigenic. Therefore, if complete separation of *Drosophila* cells and activated CD8 cells is not achieved, there is no inherent danger known to be associated with the administration of a small number of *Drosophila* cells, whereas administration of mammalian tumor-promoting cells may be hazardous.

Methods of re-introducing cellular components are used such as those exemplified in U.S. Pat. No. 4,844,893 to Honsik et al and U.S. Pat. No. 4,690,915 to Rosenberg. For example, administration of activated CD8 cells via intravenous infusion is appropriate.

EXAMPLE 3

Dendritic Cells Pulsed with the WT1 Peptide CMTWNQMNL (SEQ ID NO: 2) for Treating Breast Cancer Breast carcinoma is potentially curable only when truly localised. The most common problem is either late presentation with overt metastases or, more frequently, the development of systemic metastases after apparent local cure. Metastatic breast carcinoma is highly chemosensitive and effective chemotherapy routinely induces disease remission, allowing delay in the onset of secondary disease or amelioration of the symptoms of extensive disease.

This type or immunotherapy is based on the proposition that tumour growth and dissemination reflects a failure in immunological surveillance, either due to reduction in antigen presentation by the neoplastic cells or due to generalised decline in patient immunity. There is evidence that both mechanisms occur in breast carcinoma and in particular that there are important deficiencies in dendritic cell (DC) function (Gabrilovich et al (1997) *Clin. Cancer Res.* 3, 483-490). Cytotoxic T cell responses are demonstrated in vitro to immunogenic peptides such as the WT1 peptide CMTWNQMNL (SEQ ID NO: 2). DC are professional antigen-processing and -presenting cells which are critical to the development of primary MHC-restricted T-cell immunity. They originate from a $CD34^+$ precursor in bone marrow, but can also be derived from a post colony-forming unit $CD14^+$ intermediate in the peripheral blood. DC migrate to peripheral sites in skin, mucosa, spleen and thymus. They have been implicated in a variety of clinically important processes, including allograft rejection, atopic disorders, autoimmunity and anti-tumour immunity.

The patient is typed as HLA-A2.

DC are cultured ex vivo from $CD34^+$ stem cells or $CD14^+$ peripheral blood monocytes using cytokines, principally GM-CSF, IL4 and TNFα. DC from both these sources are immunocompetent and can take up exogenously presented antigen, process it and then present it to cytotoxic T-cells (Grabbe et al (1995) *Immunology Today* 16, 117-121; Girolomoni & Ricciardi-Castagnoli (1997) *Immunology Today* 18, 102-104). Recent studies have demonstrated that DC can transfer antigen-specific tumour immunity generated in vivo (Kwak et al (1995) *Lancet* 345, 1016-1020) and that autologous DC pulsed with tumour antigen ex vivo can induce a measurable anti-tumour effect (Hsu et al (1996) *Nature Medicine* 2, 52-58). DC can be effectively pulsed using a crude tumour membrane lysate, purified peptides or peptide fragments.

WT1 is a polypeptide expressed by breast cancers.

Keyhole limpet haemocyanin (KLH) is an immunogenic protein which is used as an innocuous positive control for the immunocompetence of the patient in studies similar to this (Hsu et al (1996) *Nature Medicine* 2, 52-58).

The feasibility of using ex vivo expanded autologous dendritic cells from patients with recurrent breast carcinoma, loaded with a purified preparation of the WT1 peptide CMTWNQMNL (SEQ ID NO:2), and reinfused as adoptive immunotherapy, is established in the following way.

The work described establishes optimal methodology for the generation of autologous DC by ex vivo expansion from peripheral blood of patients with recurrent breast carcinoma; assesses the feasibility of loading DC with exogenous WT1 peptide; examines acute tolerability and toxicity of autologous reinfusion; examines whether an immune response to the WT1 peptide or KLH develops; and examines the effect on measurable tumour bulk.

Adoptive immunotherapy is likely to prove most effective in the control or elimination of minimal residual disease rather than in the reduction of bulk disease. It is conceivable that immunotherapy may temporarily increase the dimensions of bulk disease due to influx of cytotoxic T lymphocytes. Extent and bulk of disease will be monitored following therapy but not used as a formal endpoint. Patients are followed up in the routine manner in the long term to ensure that no long term adverse events are manifest.

Dendritic Cell Culture from Normal Volunteers $CD14^+$ peripheral blood monocytes are adhered to tissue culture flasks and cultured in the presence of 1% AB serum, GM-CSF (400 ng/ml) and IL-4 (400 IU/ml) for 7 days. This yields cells with the morphology of DC and a mean of 49% with the CD1a$^+$ marker which is indicative of the immature form of the DC capable of taking up and presenting antigen. These cells are then matured to CD83$^+$ cells by the addition of TNFα (15 ng/ml), which enables the DC to present antigen to cytotoxic T-cells. 7% of the cells become CD83$^+$ within 1 day, but 3 days at least are required for maximum effect. It is possible that monocyte conditioned medium could replace the 1% AB serum.

Dendritic Cell Culture from Patients with Relapsed Breast Carcinoma

DC are generated from 6 patients with relapsed metastatic disease, both prior to and following salvage chemotherapy (a total of 12 samples of peripheral blood, each of 50 mls).

Clinical Study

Patients donate a single unit of autologous blood according to standard protocol. Patients are evaluated prior to donation by a blood transfusion service physician. Autologous donations are screened in the same way as allogeneic donations for routine virus markers (HIV, HBV, HCV and syphilis) and patients give consent to this after appropriate counseling if they wish to participate. This precaution protects clinical and laboratory staff from potential infection and the routine blood supply from the possibility of cross-contamination. The blood is taken into a routine quad-pack. This allows automated separation of red cells, buffy coat and plasma. The buffy coats yields approximately 670×10$^6$ mononuclear leukocytes which give approximately 47×10$^6$ DC using current techniques. A dosage range of 8-128×10$^6$ DC per patient is used. Peripheral blood monocytes are divided into 2 aliquots and pulsed with WT1 peptide and KLH between days 1 and 10. Serum-free culture conditions or autologous plasma is used in preference to allogeneic AB serum. Cultured DCs are pooled, washed and resuspended in 100 mls saline prior to infusion over 1 hour. The autologous red cell concentrate is not returned to the patient other than for a standard clinical indication. The ex vivo DC culture procedures are carried out following good manufacturing practices.

Patients who donated the initial blood samples will, by this time, have received salvage chemotherapy and may or may not be in clinical remission. Further patients with relapsed metastatic disease receive treatment prior to receiving chemotherapy. There are two treatment regimes:

(1) metastatic relapse, standard therapy followed by adoptive immunotherapy;
(2) metastatic relapse, adoptive immunotherapy followed by standard therapy.

Criteria to include patients for treatment are:

Patients with localised relapse or metastatic breast carcinoma.

Previous treatment with cytotoxic chemotherapy or hormonal therapy.

Evaluable disease (UICC criteria).

Survival predicted to be >12 weeks.

Fulfil criteria for autologous blood donation (including HgB>120 g/l).

Informed consent.

Age between 18 years and 70 years.

Criteria to exclude patients from treatment are:

Pregnancy.

CNS metastases.

Previous or concomitant metastases.

Unable to give informed consent.

Consent refused.

Age<18 years or >70 years.

Product infusion is carried out under the direct supervision of an experienced physician on a ward on day bed unit where resuscitation and supportive care facilities are available if required.

EXAMPLE 4

Selective Elimination of Leukemic CD34$^+$ Progenitor Cells by Cytotoxic T Lymphocytes Specific for WT1

Hematological malignancies, such as acute and chronic myeloid leukemia, are characterized by the malignant transformation of immature CD34$^+$ pregenitor cells. Transformation is associated with elevated expression of the WT1 transcription factor. Here we demonstrate that WT1 can serve as target for CTL with exquisite specificity for leukemic progenitor cells. HLA-A0201-restricted CTL specific for WT1 kill leukemia cell lines and inhibit colony formation by transformed CD34$^+$ progenitor cells isolated from CML patients, whilst colony formation by normal CD34$^+$ progenitor cells is unaffected.

Thus, the tissue-specific transcription factor WT1 is an ideal target for CTL-mediated purging of leukemic progenitor cells in vitro, and for antigen-specific therapy of leukemia and other WT1-expressing malignancies in vivo.

Cells of the hematopoietic system are derived from stem cells (HSC) capable of self renewal and differentiation. Transplantation experiments in humans and mice have shown that CD34$^+$ cell populations contain HSC capable of reconstituting the erythroid, myeloid and lymphoid lineages in myeloablated recipients [1]. In addition, HSC capable of reconstituting murine hosts were recently demonstrated in a rare population of CD34$^-$/lin$^-$ bone marrow cells [2].

There is strong evidence that the critical transformation events in (CML and AML affect immature CD34$^+$ progenitor cells. Since the majority of leukemic blast cells have limited proliferative capacity, the malignant disease must be maintained by a subpopulation of leukemic progenitor cells with extensive proliferative and self-renewal capacities [3,4]. Transplantation studies with purified cells from AML patients showed that only immature CD34$^+$ cells were capable of initiating leukemia in immunocompromised murine recipients [5]. Similarly, purified CD34$^+$ cells from CML patients efficiently initiated leukemia in murine recipients [6,7].

The molecular events leading to uncontrolled progenitor cell proliferation are not fully understood. Although BCR/ABL fusion proteins associated with the t(9;22) chromosomal translocation is the hallmark of CML, BCR/ABL transcripts can also be found in healthy individuals indicating that additional factors are required to develop leukemia [8]. The WT1 transcription factor is a candidate protein contributing to leukemogenesis. This transcription factor is normally expressed in immature CD34$^+$ progenitor cells and differentiation is associated with WT1 downregulation [9,10]. Elevated levels of WT1 expression have been observed in unseparated mononuclear cells and in purified CD34+ cells from AML and CML patients [11,12]. In vitro studies showing that increased WT1 expression can block normal differentiation and enhance proliferation of hematopoietic progenitor cells provide an explanation for the potential of WT1 to contribute to leukemogenesis [13,14].

The results of a recent study suggested that T lymphocytes specific for CD34+ progenitor cells are critically important in mediating anti-leukemic effects in CML patients [15]. In this study we explored the possibility of exploiting WT1 as a target molecule to direct cytotoxic T lymphocytes against leukemic progenitor cells. We tested the hypothesis that CML but not normal CD34+ progenitor cells express sufficient WT1 protein to trigger CTL attack.

METHODS

Cell lines: The K562 cell line was established from the pleural effusion of a female CML patient in blast crisis [16]. The BV173 cell line was established from the peripheral blood of a male CML patient in blast crisis [17]. The cell line 697 was established from the bone marrow of a 12 year old boy with acute lymphoblastic leukemia [18]. The C1R cell line is a HLA-A0201-negative EBV transformed lymphoblastoid cell line [19]. The T2 cell line has been selected for loss of the genes encoding TAP (transporter associated with antigen processing), resulting in inefficient loading of HLA class I molecules with endogenous peptides [20]. As a consequence, the HLA-A0201 molecules of T2 cells can be efficiently loaded with exogenous peptides. Drosophila cells transfected with HLA-A0201, human β-2 microglobulin, B7.1 and ICAM-1 were a kind gift from Dr. M. Jackson.

Synthetic peptides: A peptide derived from human Wilms tumour antigen 1 P126 (RMFPNAPYL; SEQ ID NO: 1) and a control HLA-A02 01-binding peptide derived from the E7 protein of human papilloma virus type 16 were synthesised by the central peptide synthesis laboratory of the Imperial College Medical School, using fluorenylmethoxycarbonyl chemistry. The quality of the peptides was assessed by HPLC analysis and the expected molecular weight was observed using matrix-assisted laser desorption mass spectrometry. The peptides were dissolved in PBS (pH 7.4) to give a concentration of 2 mM and stored at −20° C.

Generation of allo-HLA-restricted CTL lines. PBMC were separated from buffy coat packs using Ficoll gradient centrifugation and stained with monoclonal antibodies HB54 (anti-HLA-A2, B17) and HB117 (anti-HLA-A2, A28). A2-negative PBMC were used as responders. Peptide coated Drosophila cells transfected with HLA-A0201, human β2-microglobulin, B7.1 and ICAM-1 were used as initial stimulators. Drosophila cells were induced in 100 mM $CuSO_4$ for 48 hours washed three times with medium and loaded with peptide at a concentration of 100 μM for 4 hours. Each well of 24 well plate received $2\times10^6$ responder PBMC and $2\times10^5$ stimulator cells in 2 ml T cell medium. On day 5 T cells were harvested and plated in fresh T cell medium at a density of $5\times10^5$ per well with the addition of $2\times10^6$ autologous irradiated PBMC as feeders, $2\times10^5$ irradiated peptide-coated T2 cells, 10% QS4120 culture supernatant (containing anti-CD4 antibodies) and 10 U/ml hurIL-2 (Boehringer). The cultures were restimulated weekly using T2 cells coated with the immunizing peptide as stimulators. After 2-3 cycles of stimulation the bulk cultures were cloned in 96 well plates at a density of 1, 10 and 30 cells per well. $10^4$ peptide-coated T2 cells, $2\times10^5$ HLA-A2 negative PBMC feeders and 2 U/ml IL-2 were added to each well. The cytotoxicity of each well was tested against T2 target cells coated with the immunizing peptide or a control HLA-A0201-binding peptide. Peptide-specific microcultures were expanded and restimulated weekly in 24 well plates by adding $2\times10^6$ feeders, $2\times10^5$ stimulator cells and 10 U/ml IL-2. The T cell line 77 (see FIG. 4B) was Maintained for over 1 year in culture and served as source of CTL for most experiments in this study. Since this line consisted of CD4+ and CD8+ T cells, CD8+ subclones were used to show that the specific killing activity was mediated by CD8+ CTL. Unlike the parental 77 line, the in vitro life-span of CD8+ subclones was limited to a few months.

CTL assays: CTL assays were performed as described. Briefly, $10^6$ T2 cells were incubated for 1 hr in 200 μl of assay medium (RPMI 1640 with 5% heat inactivated FCS) with 100 μM synthetic peptide at 37° C. Peptide-coated T2 cells or tumour cells were $^{51}$Cr-labelled for 1 hour, washed and added to serial two-fold dilutions of effector cells in round bottom 96 well plates to obtain a total volume of 200 μl/well. Assay plates were incubated for 4 hrs at 37° C., 5% $CO_2$. 100 μl of supernatant was harvested and counted using a Wallac Gamma Counter. The specific lysis was calculated by the equation (experimental release−spontaneous release)/maximum release−spontaneous release)×100%.

Purification of hematopoietic CD34+ cells: As a source of normal CD34+ cells we used human bone marrow from adult healthy donors (n=5), leukapheresis products from stem cell mobilised solid tumor patients in disease remission (n=2) and cord blood (n=1). Samples of cord blood were obtained from discarded placental and umbilical tissues by drainage of the blood into sterile collection tubes. Informed consent for use of these cells was obtained from donors or parents as appropriate. As a source of leukemic CD34+ cells peripheral blood was obtained from CML patients in chronic phase and not treated with interferon since at least three months.

Samples were diluted 1:2 in Hanks balanced salt solution (HBSS) and enriched for mononuclear cells by density gradient centrifugation (Lymphoprep 1.077 g/ml, Nycomed, UK) and the recovered mononuclear fraction was subject to magnetic microbead selection for the isolation of CD34+ fraction, using the Minimacs system and following the manufacturer instruction (Miltenyi Biotec, UK). The purity of the cell population ranged from 80-95% as estimated by FACS analysis using an anti-human CD34 phycoerythrin (PE) mouse monoclonal antibody (Becton Dickinson).

RNA extraction and RT-PCR. Total RNA of $10^6$ cells was isolated according to RNAzol™ B protocol (AMS Bio, UK). cDNA synthesis of the whole RNA pellet was performed in a 40 μl reaction. The dissolved RNA pellet was first incubated with 2 μg oligo-dT 12-18 primer (Life Technologies, Scotland) at 65° C. for 10 min, followed by a 1 h incubation at 42° C. with a mixture of 50 U of murine leukemia virus (MuLV) reverse transcriptase, 10 mM dithiothreitol, 1 mM dNTP (Boehringer Mannheim, UK), 40 U RNase inhibitor (Promega, UK). Five μl of the cDNA preparation was used for PCR amplification in a 50 μl volume of final reaction mixture containing 2.5 U of Taq DNA polymerase (Qiagen, UK), 1 mM dNTP, 20 OD/ml primer. Amplification of the human WT1 coding region was achieved using sense primers located in exon 7 (21mer 5'-ggc atc tga gac cag tga gaa-3') (SEQ ID NO:6) and antisense primers in exon 10 (22mer 5' gag agt cag act tga aag cag t-3') (SEQ ID NO:7). Expected size for WT1 PCR product is 482 bp. RNA integrity was verified by amplifying the human c-abl gene in every sample using intron-spanning primers: 22mer sense 5'-ccc aac ctt ttc gtt gca ctg t-3' (SEQ ID NO:8); 22mer antisense 5'-cgg ctc tcg gag gag acg atg a-3' (SEQ ID NO:9). Expected size of c-abl PCR product is 385 bp. Hot-start PCR was performed for 35 cycles with a thermal cycler (Techne Genius, Cambridge) under the following conditions (same for ABL and WT1 amplification): denaturing at 95° C. for 1 min, primer annealing at 56° C. for 1 min and chain elongation at 72° C. for 2 min. The cycling was initiated by a 5 min denaturation step at 95° C. to heat inactivate the reverse transcriptase and terminated by a 10 min final extension at 72° C. All RT-PCRs were performed at least twice and negative control (no cDNA) and positive control (cDNA from the WT1 expressing leukemic cell line BV173) were included in every experiment. PCR products were electrophoresed through 1.5% agarose gels.

Western blot analysis: Separated CD34+ cells ($2 \times 10^5$ cells) were washed in PBS and lysed in Laemmli Buffer. The cell lysate was fractionated by a 12% SDS polyacrylamide gel electrophoresis (PAGE) and transferred to a nitrocellulose membrane (Amersham, UK) by wet transfer. The membrane was then blocked in PBS containing 0.01% Tween 20 and 5% nonfat dry milk for 1 h at room temperature and incubated first with rabbit anti human WT-1 C19 polyclonal antibody (Santa Cruz Calif., 1:200 in blocker) overnight at 4° C. and then with rabbit anti-actin polyclonal serum (Sigma UK, 1:500 in blocker) for 30 minutes at room temperature. The signal was revealed by incubating the membrane with horseradish peroxidase-conjugated swine anti-rabbit antibody (DAKO UK, 1:1000) and ECL reaction (Amersham UK) according to manufacturer's instructions.

Progenitor assay (CFU assay): CFU assays were performed by plating 1000-3000 CD34+ cells in methylcellulose medium supplemented with the following recombinant human growth factors (Stem Cell Technologies): stem cell factor (SCF, 50 ng/ml), interleukin-3 (IL-3, 20 ng/ml) interleukin-6 (IL-6, 20 ng/ml), granulocyte macrophage colony stimulating factor (GM-CSF, 20 ng/ml), granulocyte colony stimulating factor (G-CSF). The cultures were incubated for 14 days at 37° C. in humidified atmosphere at 5% $CO_2$ to allow the development of colony-forming units granulocyte macrophage (CFU-GM).

RESULTS

Figures 4A, 4B:
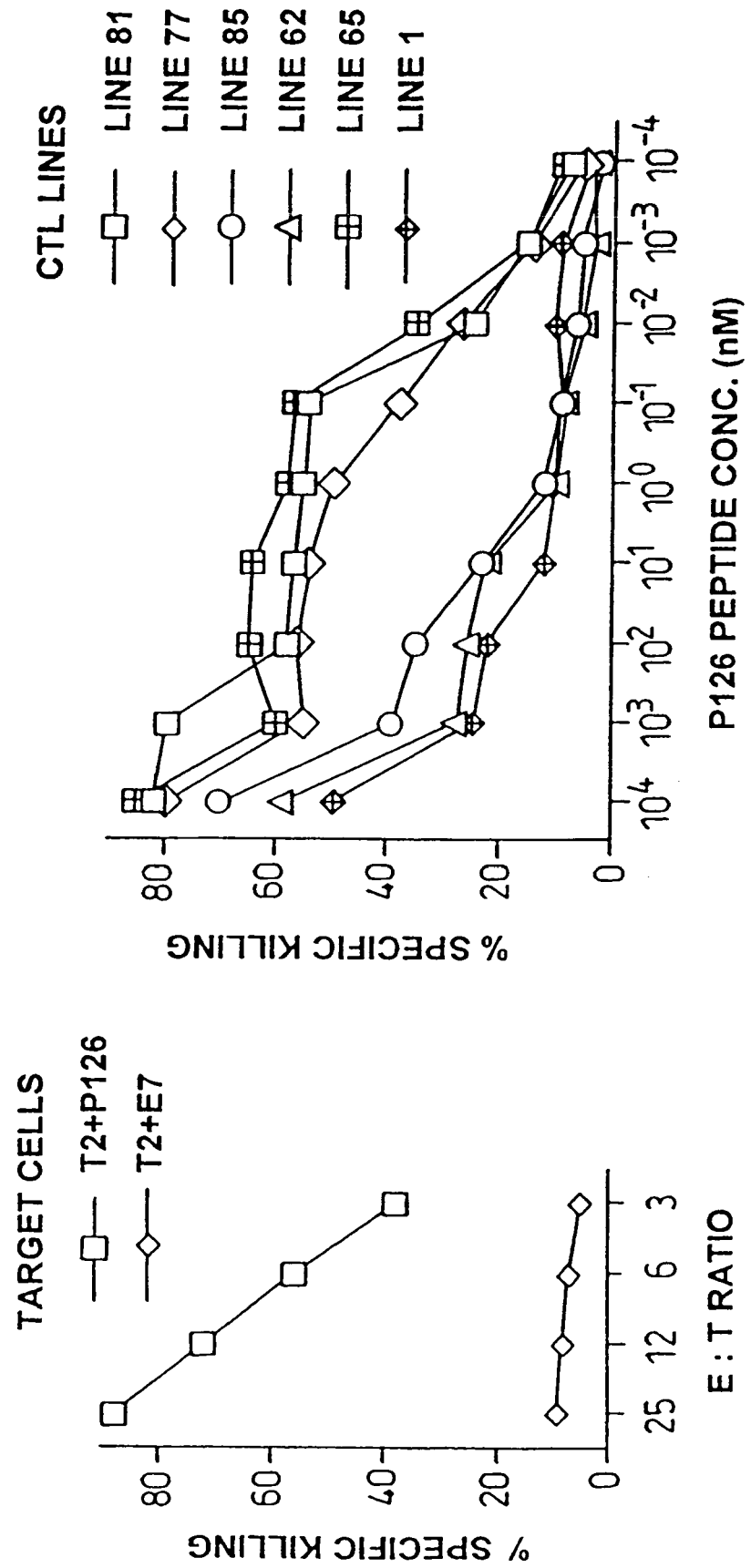

Generation of WT-1 specific CTL: Expression of the WT1 transcription factor in adults is detectable in renal podocytes, testicular Sertoli cells, ovarian granulosa cells and CD34+ bone marrow cells [21]. To avoid possible immunological tolerance to WT1 we used a previously described approach of generating peptide-specific CTL from MHC-mismatched donors. This approach is suitable for generating CTL against any protein overexpressed in tumor cells, independent of immunological tolerance [22,23]. A 9 amino acid long WT1-derived peptide epitope P126 (RMFPNAPYL (SEQ ID NO: 1) was selected as the CTL target. This peptide binds to HLA-A0201 class I molecules (see Example 1), the most frequent class I allele found in caucasian individuals. Responder lymphocytes from HLA-A0201− donors were cultured in vitro with HLA-A0201+ stimulator cells presenting the P126 peptide, and limiting dilution cultures were used to isolate peptide-specific CTL lines. Experiments with peptide-coated T2 target cells showed that the CTL were highly specific for the P126 peptide (FIG. 4A). Peptide titration indicated that the CTL could be divided into high avidity lines capable of recognising low picomolar peptide concentrations, and low avidity lines recognising low nanomolar peptide concentrations (FIG. 4B). High avidity CTL lines were selected for further experiments.

T1-specific CTL kill leukemia cell lines: Analysis of a panel of leukemia cell lines revealed that P126-specific CTL killed the HLA-A0201+ cells BV173 and 697 (FIG. 4C). The HLA-A0201 leukemia cell line K562 was only killed after transfection with HLA-A0201. In contrast, the HLA-A0201+ EBV-transformed B cell line C1R-A2 was not killed, unless cells were coated with P126 peptides (FIG. 4C; similar results were seen with other EBV transformed cells). The expression of WT1 in the CTL target cells was analyzed at the RNA and protein level. RT-PCR demonstrated that the leukemia cell lines, but not the EBV-transformed C1R-A2 cells, expressed WT1 RNA (FIG. 5A). Similar results were obtained by Western blotting showing that WT 1 protein was only expressed in leukemia cells but not C1R-A2 (FIG. 5C). Together, the data indicated that the CTL recognised A0201+ leukemia cell lines, and that CTL killing correlated with WT1 expression.

Figure 6A:
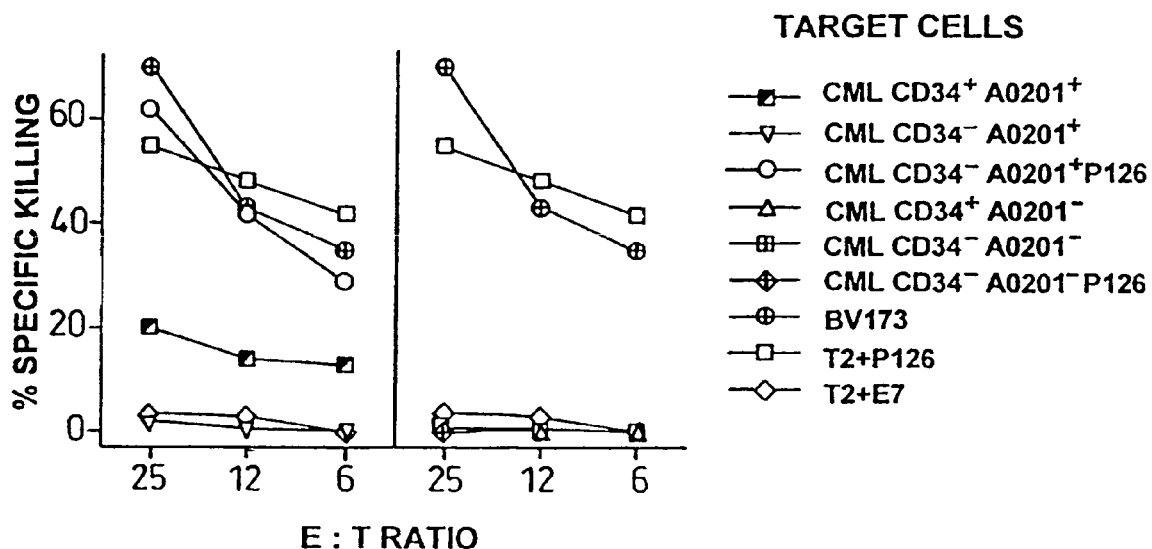

WT1-specific CTL kill fresh leukemic CD34+ cells: Mononuclear cells from peripheral blood of CML patients in chronic phase were separated into immature CD34+ and mature CD34− populations. As expected, cells isolated from HLA-A0201− patients were not recognised by P126-specific CTL (FIG. 6A). When cells from HLA-A0201+ CML patients were analyzed, the CTL selectively recognised the CD34+ cell population, Whilst no killing of the more mature CD34− population was observed (FIG. 6A). Lack of killing of CD34− cells was most likely due to insufficient expression of the WT1-derived target peptide, since coating of these cells with exogenous P126 peptide resulted in CTL killing (FIG. 6A). RT-PCR analysis revealed strong WT1 RNA expression in CD34+ cells and low expression in CD34− cells (FIG. 5B). WT1 protein expression detectable by Western blotting was restricted to CD34+ and no protein was detectable in CD34− cells (FIG. 5C). Both RT-PCR and Western analysis showed variation in the level of WT1 expression in leukemic CD34+ cell populations. Thus, we explored whether the observed variation in the level of WT1 expression resulted in a variation in the level of CTL killing. However, analysis of 11 different CML patients showed that the CTL consistently lysed approximately 20% (SD 5%) of the CD34+ population (FIG. 5B). This result raised the possibility that WT1 expression was restricted to a subpopulation of approximately 20% of CD34+ cells, and that the expression level in all 11 CML patients was sufficient to render most of these cells susceptible to CTL killing. Thus, we explored whether the subpopulation recognised by CTL included the clonogenic progenitor cells that can give raise to colonies of the granulocyte/macrophage lineage. Indeed, when CD34+ populations isolated from 9 CML patients were treated with P126-specific CTL this resulted in 80-100% inhibition of colony formation (FIG. 5D). This indicated that the majority of colony forming progenitor cells were removed by P126-specific CTL. The 'escape' colonies seen in CTL treated samples were small when compared to the colonies in untreated samples. This is consistent with the possibility that the 'escape' colonies were derived from progenitor cells that had already initiated differentiation towards the granulocyte/myeloid lineage which is associated with down-regulation of WT1 expression. Such partially differentiated progenitors might escape recognition by WT1-specific CTL, and the small size of the colonies observed in the CFU assay might reflect the reduced clonal burst size of these progenitors.

Importantly, colony-formation by CD34+ cells from HLA-A0201− CML patients was unaffected, indicating that the elimination of progenitors with colony forming activity was dependent upon HLA-restricted antigen recognition by the CTL.

Figure 6B:
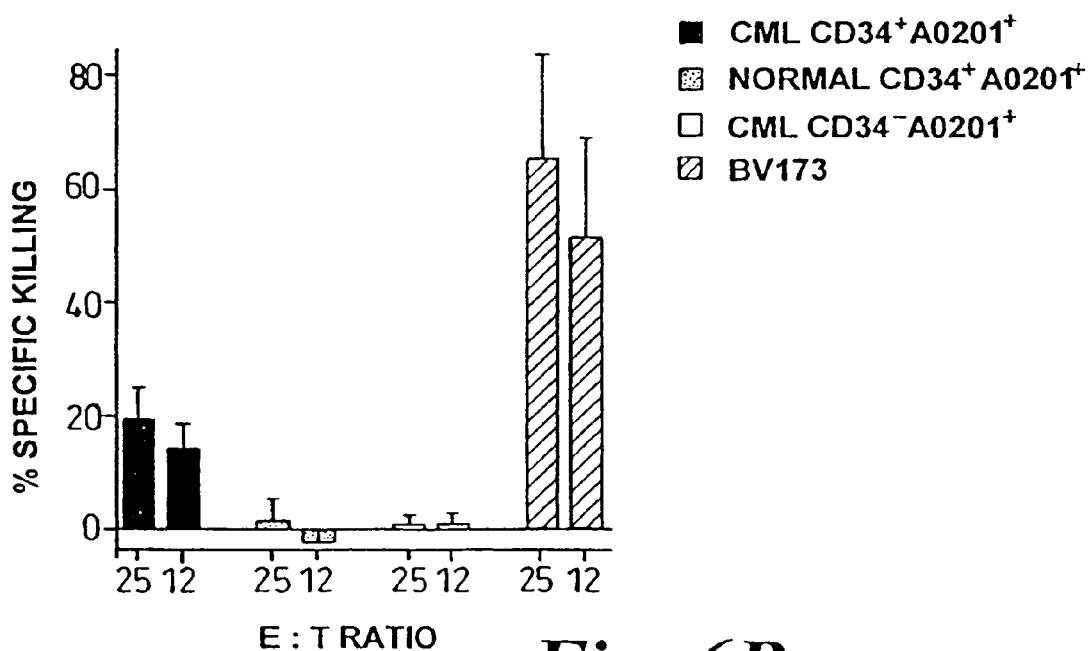
Figure 6C:
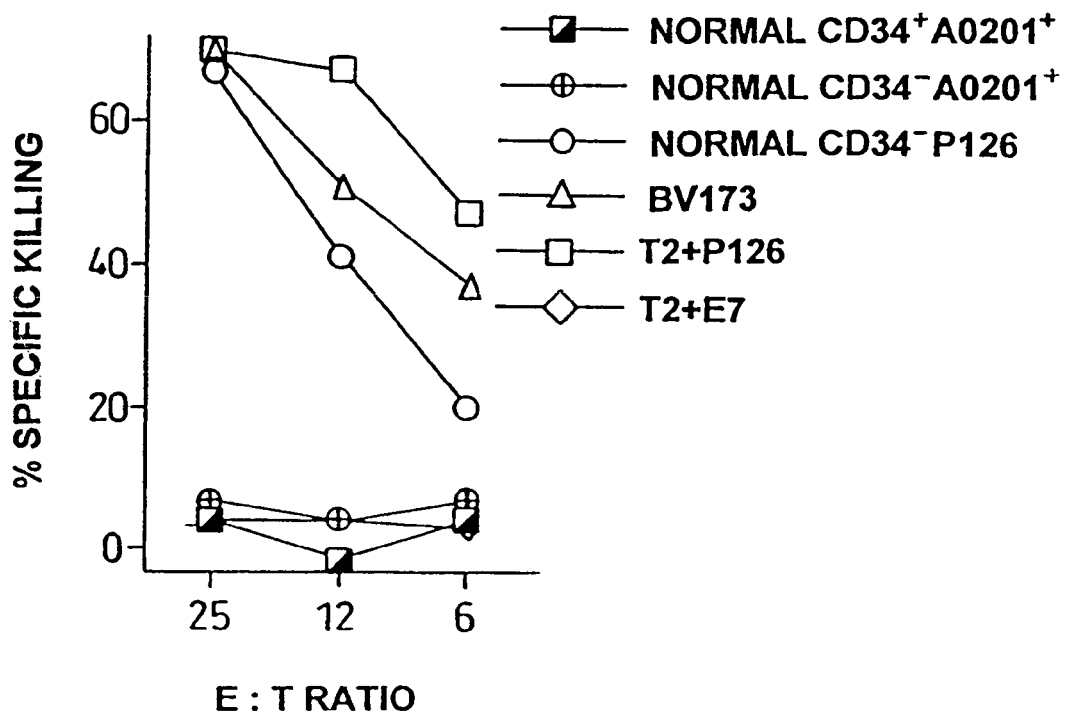
Figure 6D:
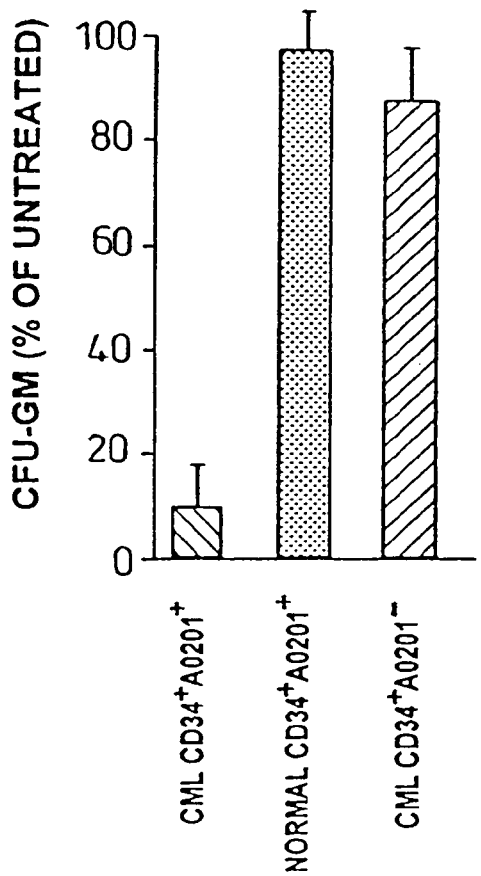
Figure 6E:
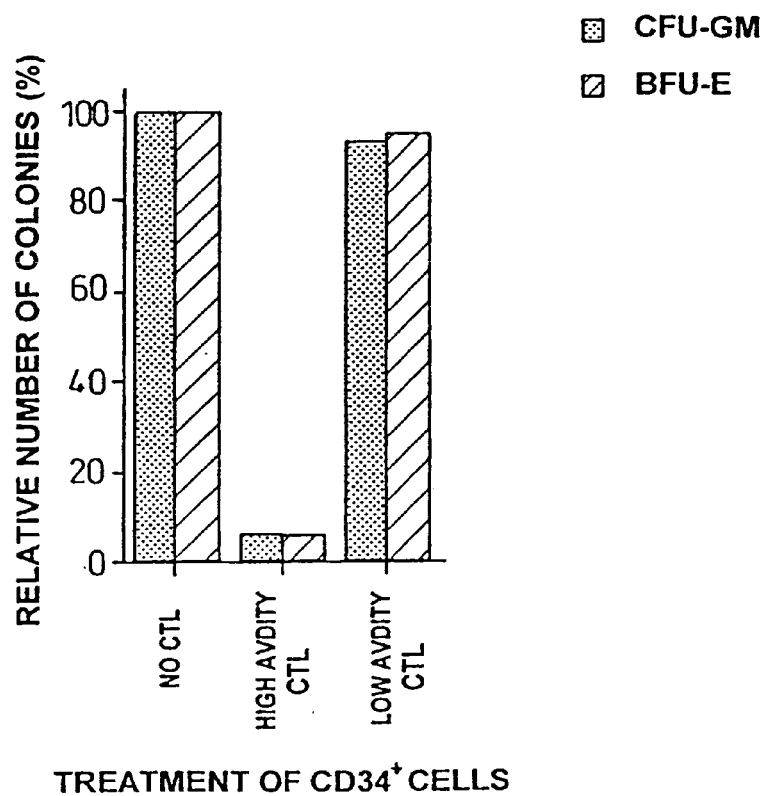
Figure 6F:
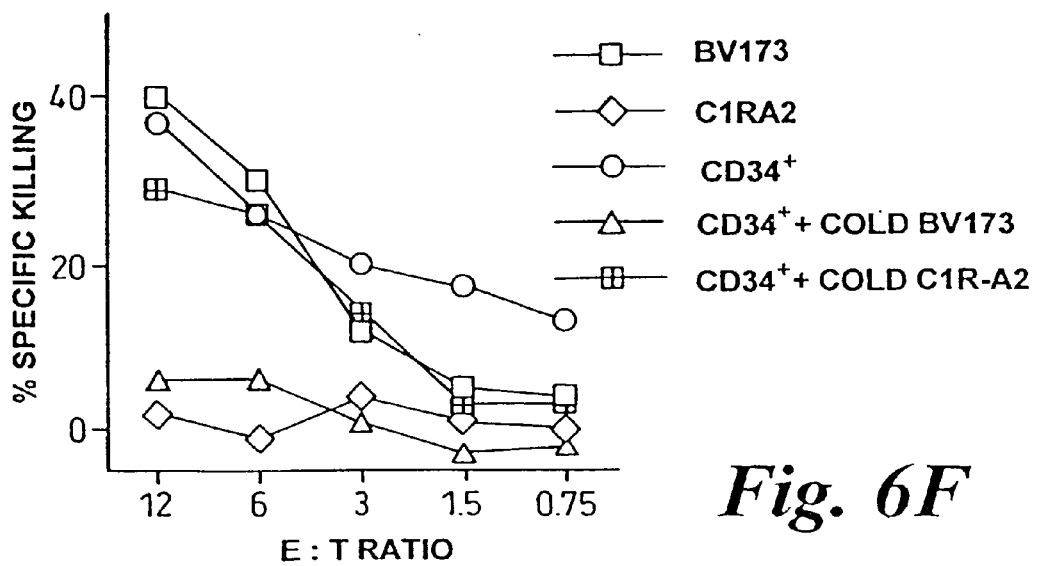

Finally, we explored whether CTL discriminated between leukemic and normal CD34+ progenitor cells. Normal CD34+ cells were isolated from bone marrow, peripheral blood or umbilical cord blood of HLA-A0201+ donors and used as CTL targets. Independent of the source of CD34+ cells, anti-P126 CTL did not inhibit colony formation by these cells (FIG. 5D). Furthermore, normal CD34+ cells were not killed when used as targets in cytotoxicity assays (FIGS. 6B and C). The selective CTL killing of leukemic versus normal CD34+ cells can be explained by differences in WT1 expression. WT1 RNA expression was higher in leukemic compared with normal CD34+ cells (FIG. 5B), and Western blot analysis detected WT1 protein only in leukemic but not normal CD34+ cell populations (FIG. 5C).

The infusion of donor lymphocytes (DLI) to patients in relapse after previous allogeneic stem cell transplantation can engender strong graft-versus-leukemia effects (GVL) [24,25]. A recent study showed that complete remission in CML patients undergoing DLI was associated with an increased frequency of T cells recognising leukemic CD34+ progenitor cells [15]. In contrast, T cell recognition of more mature CD34− cells in CML patients was not associated with favorable clinical response. This suggested that T lymphocytes with specificity for CD34+ CML progenitor cells were critically important in mediating anti-leukemic effects in vivo. However, there is currently no information concerning the nature of target antigens that can direct T cell responses selectively against leukemic CD34+ progenitor cells.

In order to identify such antigens we used the allo-restricted CTL approach that, independent of immunological tolerance, is suitable for raising CTL against any protein that is expressed at elevated levels in transformed cells [22,23,26]. Since the triggering of the cytotoxic effector function is a threshold phenomenon, it is possible to select CTL which are only triggered by elevated target protein levels in transformed cells but not by physiological levels of protein in normal cells [23].

There is evidence of overexpression of WT1 in leukemic CD34+ cells [12]. Elevated WT1 expression can contribute to transformation [13,14]. Normal WT1 expression is restricted to a small number of cells in postnatal life [21]. In addition to leukemia, elevated WT1 expression has also been observed in renal cell carcinoma, ovarian cancer, advanced breast cancer and in melanoma [27-30]. Therefore, CTL selectively recognising WT1 overexpressing malignant cells are invaluable reagents for antigen-specific therapy of leukemia as well as other more common malignancies. Furthermore, tumor escape by downregulation of WT1 expression is unlikely to occur if overexpression is required to maintain the transformed phenotype [31-33].

The allo-restricted CTL described here were isolated from HLA-A0201− donors and they were specific for leukemic progenitor cells presenting the WT1-derived P126 peptide in the context of HLA-A0201 class I molecules. The P126 peptide is highly immunogenic since in vitro stimulation of lymphocytes from different HLA-A0201− donors consistently induced peptide-specific, HLA-A0201-restricted CTL. Therefore, P126-specific CTL are novel reagents for antigen-specific therapy of HLA-A0201+ leukemia patients undergoing stem cell transplantation from donors displaying a one locus HLA-mismatch involving the HLA-A0201 allele. A one locus HLA mismatch is clinically acceptable as demonstrated in a recent study showing comparable prognosis in leukemia patients receiving transplants from one-locus-mismatched and HLA-matched unrelated donors [34]. Thus, a one-locus-mismatch transplant provides an ideal setting for antigen-specific therapy with allo-restricted CTL derived from the donor. The in vitro stimulation protocol described here in combination with selection of relevant CTL by staining with HLA-A0201 tetramers containing P126 peptides will allow rapid isolation of P126-specific CTL for adoptive therapy.

In addition, it is possible that WT1 can be exploited for antigen-specific therapy in the autologous setting. This is supported by our observation that P126-specific CTL can be isolated from HLA-A0201+ donors. Since WT1 expression in adults is restricted to a relatively small number of cells (e.g. CD34+ bone marrow cells, renal podocytes, testicular Sertoli cells and ovarian granulosa cells) tolerance of autologous T lymphocytes to WT1 is probably incomplete. Therefore, it may be possible to exploit the identified P126 epitope for the design of anti-WT1 vaccine preparations aimed at stimulating CTL responses against leukemia and other malignancies with elevated WT1 expression such as renal cell carcinoma, ovarian cancer, melanoma and breast cancer.

In addition to in vivo therapy, the WT1-specific CTL provide a tool for in vitro purging of autologous bone marrow cells harvested from leukemia patients. The CTL removed leukemic progenitors of the granulocyte/macrophage lineage (FIG. 6D) and also progenitors of the erythroid lineage (not shown). In contrast, the CTL did not recognise normal progenitors of the three lineages. The selective removal of transformed CD34+ progenitor cells should reduce the risk of reinfusing leukemic progenitor cells, thus overcoming a major limitation of autologous stem cell transplantation [35].

To date, tissue-specific minor histocompatibility antigens and lineage-specific antigens, such as proteinase 3, have been studied as potential targets for leukemia-reactive CTL [36-39]. The WT-1 transcription factor is the first target antigen capable of directing CTL responses selectively against leukemic progenitor cells.

REFERENCES FOR EXAMPLE 4

1. DiGiusto D, Chen S, Combs J, Webb S, Namikawa R, Tsukamoto A, Chen B P, Galy A H: Human fetal bone marrow early progenitors for T, B, and myeloid cells are found exclusively in the population expressing high levels of CD34. Blood 84:421-32, 1994
2. Bhatia M, Bonnet D, Murdoch B, Gan O I, Dick J E: A newly discovered class of human hematopoietic cells with SCID-repopulating activity. Nature Medicine 4:1038-45, 1998
3. McCulloch E A: Stem cells in normal and leukemic hemopoiesis (Henry Stratton Lecture, 1982). Blood 62:1-13, 1983
4. Griffin J D, Lowenberg B: Clonogenic cells in acute myeloblastic leukemia. Blood 68:1185-95, 1986
5. Bonnet D, Dick J E: Human acute myeloid leukemia is organized as a hierarchy that originates from a primitive hematopoietic cell. Nat Med 3:730-7, 1997
6. Wang J C, Lapidot T, Cashman J D, Doedens M, Addy L, Sutherland D R, Nayar R, Laraya P, Minden M, Keating A, Eaves A C, Eaves C J, Dick J E: High level engraftment of NOD/SCID mice by primitive normal and leukemic hematopoietic cells from patients with chronic myeloid leukemia in chronic phase. Blood 91:2406-14, 1998
7. Dazzi F, Capelli D, Hasserjian R, Cotter F, Corbo M, Poletti A, Chinswangwatanakul W, Goldman J M, Gordon M Y: The kinetics and extent of engraftment of chronic myelogenous leukemia cells in non-obese diabetic/severe combined immunodeficiency mice reflect the phase of the 7. donor's disease: an in vivo model of chronic myelogenous leukemia biology. Blood 92:1390-6, 1998
8. Bose S, Deininger M, Gora Tybor J, Goldman J M, Melo J V: The presence of typical and atypical BCR-ABL fusion genes in leukocytes of normal individuals: biologic significance and implications for the assessment of minimal residual disease. Blood 92:3362-7, 1998
9. Maurer U, Brieger J, Weidmann E, Mitrou P S, Hoelzer D, Bergmann L: The Wilms' tumor gene is expressed in a subset of CD34+progenitors and downregulated early in the course of differentiation in vitro. Exp Hematol 25:945-50, 1997
10. Baird P N, Simmons P J: Expression of the Wilms' tumor gene (WT1) in normal hemopoiesis. Exp Hematol 25:312-20, 1997
11. Inoue K, Sugiyama H, Ogawa H, Nakagawa M, Yamagami T, Miwa H, Kita K, Hiraoka A, Masaoka T, Nasu K, et al.: WT1 as a new prognostic factor and a new marker for the detection of minimal residual disease in acute leukemia. Blood 84:3071-9, 1994
12. Inoue K, Ogawa H, Sonoda Y, Kimura T, Sakabe H, Oka Y, Miyake S, Tamaki H, Oji Y, Yamagami T, Tatekawa T, Soma T, Kishimoto T, Sugiyama H: Aberrant overexpression of the Wilms tumor gene (WT1) in human leukemia. Blood 89:1405-12, 1997
13. Inoue K, Tamaki-H, Ogawa H, Oka Y, Soma T, Tatekawa T, Oji Y, Tsuboi A, Kim E H, Kawakami M, Akiyama T, Kishimoto T, Sugiyama H: Wilms' tumor gene (WT1) competes with differentiation-inducing signal in hematopoietic progenitor cells. Blood 91:2969-76, 1998
14. Svedberg H, Chylicki K, Baldetorp B, Rauscher FJr, Gullberg U: Constitutive expression of the Wilms' tumor gene (WT1) in the leukemic cell line U937 blocks parts of the differentiation program. Oncogene 16:925-32, 1998
15. Smit W M, Rijnbeek M, van Bergen C A, Fibbe W E, Willemze R, Falkenburg J H: T cells recognizing leukemic CD34(+) progenitor cells mediate the antileukemic effect of donor lymphocyte infusions for relapsed chronic myeloid leukemia after allogeneic stem cell transplantation. Proc. Natl. Acad. Sci. USA 95:10152-157, 1998
16. Lozzio C B, Lozzio B B: Human chronic myelogenous leukemia cell-line with positive Philadelphia chromosome. Blood 45:321-34, 1975
17. Pegoraro L, Matera L, Ritz J, Levis A, Palumbo A, Biagini G: Establishment of a Ph1-positive human cell line (BV173). J Natl Cancer Inst 70:447-53, 1983
18. Findley H W, Jr., Cooper M D, Kim T H, Alvarado C, Ragab A H: Two new acute lymphoblastic leukemia cell lines with early B-cell phenotypes. Blood 60:1305-9, 1982
19. Zemmour J, Little A M, Schendel D J, Parham P: The HLA-A,B 'negative' mutant cell line CIR expresses a novel HLA-B35 allele which also has a point mutation in the translation initiation codon. J. Immunol. 148:1941-1948, 1992
20. DeMars R, Chang C C, Shaw S, Reitnauer P J, Sondel P M: Homozygous deletion that simultaneously eliminate expression of class I and class II antigens of EBV-transformed B-lymphoblastoid cells. I. Reduced proliferative responses of autologous and allogeneic T cells to mutant cells that have decreased expression of class II antigens. Hum. Immunol. 11:77-97, 1984
21. Menke A L, van der E b A J, Jochemsen A G: The Wilms' tumor 1 gene: oncogene or tumor suppressor gene? Int Rev Cytol 181:151-212, 1998
22. Stauss H J: Immunotherapy with CTL restricted by non-self MHC. Immunology Today 20:180-83, 1999
23. Sadovnikova E, Stauss H J: Peptide-specific cytotoxic T lymphocytes restricted by nonself major histocompatibility complex class I molecules: reagents for tumor immunotherapy. Proc-Natl-Acad-Sci-U-S-A 93:13114-8, 1996
24. Kolb H J, Mittermuller J, Clemm C, Holler E, Ledderose G, Brehm G, Heim M, Wilmanns W: Donor leukocyte transfusions for treatment of recurrent chronic myelogenous leukemia in marrow transplant patients. Blood 76:2462-5, 1990
25. Dazzi F, Goldman J M: Adoptive immunotherapy following allogeneic bone marrow transplantation. Annu Rev Med 49:329-40, 1998
26. Sadovnikova E, Jopling L A, Soo K S, Stauss H J: Generation of human tumor-reactive cytotoxic T cells against peptides presented by non-self HLA class I molecules. Eur J Immunol 28:193-200, 1998
27. Campbell C E, Kuriyan N P, Rackley R R, Caulfield M J, Tubbs R, Finke J, Williams B R: Constitutive expression of the Wilms tumor suppressor gene (WT1) in renal cell carcinoma. Int J Cancer 78:182-8, 1998
28. Viel A, Giannini F, Capozzi E, Canzonieri V, Scarabelli C, Gloghini A, Boiocchi M: Molecular mechanisms possibly affecting WT1 function in human ovarian tumors Int J Cancer 57:515-21, 1994
29. Silberstein G B, Van Horn K, Strickland P, Roberts C T, Jr., Daniel C W: Altered expression of the WT1 wilms tumor suppressor gene in human breast cancer. Proc Natl Acad Sci USA 94:8132-7, 1997
30. Rodeck U, Bossler A, Kari C, Humphreys C W, Gyorfi T, Maurer J, Thiel E, Menssen H D: Expression of the wt1 Wilms' tumor gene by normal and malignant human melanocytes. Int J Cancer 59:78-82, 1994
31. Algar E M, Khromykh T, Smith S I, Blackburn D M, Bryson G J, Smith P J: A WT1 antisense oligonucleotide inhibits proliferation and induces apoptosis in myeloid leukaemia cell lines. Oncogene 12:1005-14, 1996
32. Yamagami T, Sugiyama H, Inoue K, Ogawa H, Tatekawa T, Hirata M, Kudoh T, Akiyama T, Murakami A, Maekawa T: Growth inhibition of human leukemic cells by WT1 (Wilms tumor gene) antisense oligodeoxynucleotides: implications for the involvement of WT1 in leukemogenesis. Blood 87:2878-84, 1996
33. Osaka M, Koami K, Sugiyama T: WT1 contributes to leukemogenesis: expression patterns in 7,12-dimethylbenzanthracene (DMBA)—induced leukemia. Int J Cancer 72:696-9, 1997
34. Petersdorf E W, Gooley T A, Anasetti C, Martin P J, Smith A G, Mickelson E M, Woolfrey A E, Hansen J A: Optimizing outcome after unrelated marrow transplantation by comprehensive matching of HLA class I and II alleles in the donor and recipient. Blood 92:3515-20, 1998
35. O'Brien S G, Goldman J M: Current approaches to hematopoietic stem-cell purging in chronic myeloid leukemia [editorial]. J Clin Oncol 13:541-6, 1995
36. den Haan J M, Meadows L M, Wang W, Pool J, Blokland E, Bishop T L, Reinhardus C, Shabanowitz J, Offringa R, Hunt D F, Engelhard V H, Goulmy E: The minor histocompatibility antigen HA-1: a diallelic gene with a single amino acid polymorphism. Science 279:1054-7, 1998
37. Simpson E, Roopenian D, Goulmy E: Much ado about minor histocompatibility antigens. Immunol Today 19:108-12, 1998
38. Warren E H, Gavin M, Greenberg P D, Riddell S R: Minor histocompatibility antigens as targets for T-cell therapy after bone marrow transplantation. Curr Opin Hematol 5:429-33, 1998
39. Molldrem J J, Clave E, Jiang Y Z, Mavroudis D, Raptis A, Hensel N, Agarwala V, Barrett A J: Cytotoxic T-lymphocytes specific for a nonpolymorphic proteinase-3 peptide preferentially inhibit chronic myeloid-leukemia colony-forming-units. Blood 90:2529-2534, 1997

The invention claimed is:

1. A peptide derived from the amino acid sequence of human WT-1 polypeptide having at least 9 but fewer than 100 amino acids, wherein the peptide comprises the amino acid sequence RMFPNAPYL (SEQ ID NO:1), and wherein the peptide is processed by HLA-A0201-positive antigen presenting cells (APC) to produce the HLA-A0201 bound RMFPNAPYL (SEQ ID NO:1) sequence.

2. The peptide according to claim 1 wherein the peptide is processed by HLA-A0201-positive antigen presenting cells (APC) to produce the sequence RMFPNAPYL (SEQ ID NO:1) that is capable of eliciting the production of a cytotoxic lymphocyte (CTL), wherein the CTL recognizes a HLA-AA0201-positive cell which aberrantly expresses intact human WT-1 protein.

3. The peptide according to claim 1 consisting of the amino acid sequence RMFPNPAPYL (SEQ ID NO:1).

4. A composition comprising the peptide of claim 1 and a pharmaceutically acceptable carrier.

* * * * *

UNITED STATES PATENT AND TRADEMARK OFFICE
CERTIFICATE OF CORRECTION

PATENT NO. : 7,326,767 B1  
APPLICATION NO. : 09/625963  
DATED : February 5, 2008  
INVENTOR(S) : Hans Josef Stauss et al.

Page 1 of 1

It is certified that error appears in the above-identified patent and that said Letters Patent is hereby corrected as shown below:

Column 36, line 23, (Claim 2, line 6), "HLA-AA0201-positive" should read --HLA-A0201-positive--.

Column 36, line 26, (Claim 3, line 2), "RMFPNPAPYL" should read --RMFPNAPYL--.

Signed and Sealed this

Fifteenth Day of July, 2008

JON W. DUDAS  
*Director of the United States Patent and Trademark Office*